United States Patent
O'Hara

(10) Patent No.: US 11,205,500 B2
(45) Date of Patent: Dec. 21, 2021

(54) SYSTEMS AND METHODS FOR CHARACTERIZATION OF VIABILITY AND INFECTION RISK OF MICROBES IN THE ENVIRONMENT

(71) Applicant: The Joan & Irwin Jacobs Technion—Cornell Institute, New York, NY (US)

(72) Inventor: Niamh B. O'Hara, Ridgewood, NY (US)

(73) Assignee: The Joan & Irwin Jacobs Technion-Cornell Institute, New York, NY (US)

(*) Notice: Subject to any disclaimer, the term of this patent is extended or adjusted under 35 U.S.C. 154(b) by 524 days.

(21) Appl. No.: 16/083,675

(22) PCT Filed: Mar. 10, 2017

(86) PCT No.: PCT/US2017/021865
§ 371 (c)(1),
(2) Date: Sep. 10, 2018

(87) PCT Pub. No.: WO2017/156431
PCT Pub. Date: Sep. 14, 2017

(65) Prior Publication Data
US 2019/0087533 A1 Mar. 21, 2019

Related U.S. Application Data

(60) Provisional application No. 62/306,969, filed on Mar. 11, 2016.

(51) Int. Cl.
*G16B 5/00* (2019.01)
*G16B 30/00* (2019.01)
(Continued)

(52) U.S. Cl.
CPC ............... *G16B 5/00* (2019.02); *C12Q 1/689* (2013.01); *C12Q 1/6888* (2013.01);
(Continued)

(58) Field of Classification Search
CPC .......... G16B 5/00; G16B 99/00; G16B 40/00; G16B 20/00; G16B 50/00; G16B 30/00;
(Continued)

(56) References Cited

U.S. PATENT DOCUMENTS

| 2003/0148292 | A1* | 8/2003 | Messier | ............... | C12Q 1/6888 435/6.14 |
| 2010/0035232 | A1* | 2/2010 | Ecker | ...................... | C12Q 1/68 435/5 |
| 2014/0343868 | A1* | 11/2014 | Colwell | ................. | G16B 30/00 702/20 |

FOREIGN PATENT DOCUMENTS

WO    WO-2016-011086 A2    1/2016

OTHER PUBLICATIONS

International Search Report and Written Opinion dated Jul. 17, 2017 for International Application No. PCT/US2017/021865, filed Mar. 10, 2017.

* cited by examiner

*Primary Examiner* — Robert G Bachner
(74) *Attorney, Agent, or Firm* — Munel Liberto; Mintz Levin Cohn Ferris Glovsky and Popeo, P.C.

(57) ABSTRACT

The present invention relates to the use of next generation technologies coupled with viability and pathogenicity profiles to determine the threat of microbes in the environment. The invention relates to methods for identifying a pathogenicity and viability profile of microbes from collected samples.

26 Claims, 5 Drawing Sheets

(51) Int. Cl.
  *C12Q 1/6888* (2018.01)
  *C12Q 1/689* (2018.01)
  *G16B 99/00* (2019.01)
  *C12Q 1/6893* (2018.01)
  *C12Q 1/6895* (2018.01)
  *C12Q 1/70* (2006.01)
  *G16H 50/20* (2018.01)
  *G16B 25/10* (2019.01)
  *G16B 30/10* (2019.01)
  *G16B 30/20* (2019.01)
  *G16B 40/00* (2019.01)
  *G16B 20/00* (2019.01)
  *G16B 50/00* (2019.01)
  *G06N 7/00* (2006.01)

(52) U.S. Cl.
  CPC .......... *C12Q 1/6893* (2013.01); *C12Q 1/6895* (2013.01); *C12Q 1/701* (2013.01); *G06N 7/005* (2013.01); *G16B 20/00* (2019.02); *G16B 25/10* (2019.02); *G16B 30/00* (2019.02); *G16B 30/10* (2019.02); *G16B 30/20* (2019.02); *G16B 40/00* (2019.02); *G16B 50/00* (2019.02); *G16B 99/00* (2019.02); *G16H 50/20* (2018.01); *C12Q 2600/112* (2013.01); *C12Q 2600/156* (2013.01); *C12Q 2600/158* (2013.01); *Y02A 50/30* (2018.01)

(58) Field of Classification Search
  CPC ...... G16H 50/20; C12Q 1/701; C12Q 1/6895; C12Q 1/6893; C12Q 1/6888; C12Q 1/689; C12Q 2600/112; C12Q 2600/156; C12Q 2600/158; G06N 7/005; Y02A 50/30

See application file for complete search history.

SYSTEMS AND METHODS FOR CHARACTERIZATION OF VIABILITY AND INFECTION RISK OF MICROBES IN THE ENVIRONMENT

CROSS-REFERENCE TO RELATED APPLICATIONS

This application is a national stage entry, filed under 35 U.S.C. § 371, of International Application No. PCT/US2017/021865, filed on Mar. 10, 2017, which claims priority to U.S. Provisional Patent Application No. 62/306,969 filed Mar. 11, 2016, the contents of which are hereby fully incorporated by reference.

FIELD OF THE INVENTION

The present invention relates to a system and methods for the characterization of single or mixed-microorganismal samples collected from the environment or patient samples, specifically related to characterizing the viability and risk of infection of organisms in said sample. In particular, this invention relates to methods of characterizing DNA sequence data by calculating population genetic estimates, sometimes at multiple time points, to determine viability, as well as comparison of identified microbes to genomic and pathogenicity databases to calculate ratio of pathogenic versus non-pathogenic strains to model risk of infection.

BACKGROUND OF THE INVENTION

Hospital acquired infections are a common cause of morbidity and mortality in the US. An estimated $10 billion in direct costs is spent on solving this problem. Environmental testing of microbes within the hospital is severely limited. There is an urgent need for technology which can rapidly identify microbes in the environment and determine their viability and pathogenicity.

SUMMARY OF INVENTION

The present invention features methods for characterizing the viability of microbes within the environment and determining their risk of infection. The present invention features methods of characterizing DNA sequence data by calculating population genetic estimates, sometimes at multiple time points, to determine viability, as well as comparison of identified microbes to genomic and pathogenicity databases to calculate the ratio of pathogenic versus non-pathogenic strains to model risk of infection.

In an aspect, the present invention provides a method of characterizing risk of transmission and infection from one or more microorganism populations, that includes the steps of: obtaining a sample including one or more microorganism populations; determining a DNA sequence of one or more genomic DNA regions from the one or more microorganism populations; comparing the DNA sequence of the one or more genomic DNA regions to a reference database to identify the one or more microorganisms and to determine pathogenicity or non-pathogenicity of the one or more microorganisms in the sample; modeling the DNA sequence of the one or more genomic DNA regions data using Bayesian models to assess risk of transmission and infection based on the ratio of non-pathogenicity versus pathogenicity of the one or more microorganisms, wherein the Bayesian model incorporates one or more variables selected from the group consisting of environmental factors, patient medical records, and infection rates; and implementing a containment protocol based on the pathogenicity assessment.

In an embodiment, the one or more microorganism populations are selected from the group consisting of bacteria, fungi, viruses, protozoans, and parasites.

In an embodiment, bacteria are selected from the phylogenetic group consisting of Acidobacteria, Actinobacteria, Aquificae, Armatimonadetes, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermomicrobia, Thermotogae, and Verrucomicrobia.

In an embodiment, the bacteria are selected from the group consisting of *Actinomyces israelii, Bacillus anthracia, Bacillus cereus, Bacteroides fragilis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Ehrlichia canis, Ehrlichia chaffeensis, Enterococcus faecalis, Enterococcus faecium, Escherichia coli, Francisella tularensis, Haemophilus influenzae, Helicobacter pylori, Klebsiella pneumoniae, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Shigella dysenteriae, Staphylococcus aureus, Staphylococcus epidermidis, Staphylococcus saprophyticus, Streptococcus agalactiae, Streptococcus pneumoniae, Streptococcus pyogenes, Streptococcus viridans, Treponema pallidum, Ureaplasma urealyticum, Vibrio cholera, Yersinia pestis, Yersinia enterocolitica,* and *Yersinia pseudotuberculosis*.

In an embodiment, the virus are selected from the group consisting of Adenovirus, Herpes simplex, type 1, Herpes simplex, type 2, Varicella-zoster virus, Epstein-barr virus, Human cytomegalovirus, Human herpesvirus, type 8, Human papillomavirus, BK virus, JC virus, Smallpox, Hepatitis B virus, Parvovirus B19, Human astrovirus, Norwalk virus, coxsackievirus, hepatitis A virus, poliovirus, rhinovirus, Hepatitis C virus, yellow fever virus, dengue virus, West Nile virus, TBE virus, Rubella virus, Hepatitis E virus, Human immunodeficiency virus (HIV), Influenza virus, Lassa virus, Crimean-Congo hemorrhagic fever virus, Hantaan virus, Ebola virus, Marburg virus, Measles virus, Mumps virus, Parainfluenza virus, Respiratory syncytial virus, Rabies virus, Rotavirus, Orbivirus, Coltivirus, Banna virus, and zika virus.

In an embodiment, the fungi are selected from the group consisting of *Candida species, Candida albicans, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii, Pneumocystis carinii,* and *Stachybotrys chartarum*.

In an embodiment, the protozoa are selected from the group consisting of *Entamoeba histolytica, Entamoeba coli, Entamoeba dispar, Entamoeba moshkovskii, Entamoeba* bangladeshi, Entamoeba hartmanni, Dientamoeba fragilis, Endolimax nana, Iodamoeba butschlii, Plasmodium malariae, Plasmodium falciparum, Plasmodium vivax, Plasmodium ovale, Naegleria fowleri, Acanthamoeba species, Balamuthia mandrillaris, Sappinia diploidea, Giardia lamblia, Giardia intestinalis, Giardia duodenalis, Toxoplasma gondii, Nippostrongylus brasiliensis, Cryptosporidium parvum, Cryptosporidium hominis, Cryptosporidium canis, Cryptosporidium felis, Cryptosporidium meleagridis, Cryptosporidium muris, Trichomonas vaginalis, Trypanosoma cruzi, Leishmania major, Leishmania tropica, Leishmania barziliensis, Leishmania mexicana, Leishmania guyanesis, Leishmania panamensis, and Trypanosoma brucei.

In an embodiment, the DNA sequence of a plurality of genomic DNA fragments is obtained by massively parallel signature sequencing, Polony sequencing, 454 pyrosequencing, Illumina sequencing, SOLiD sequencing, ion semiconductor sequencing, DNA nanoball sequencing, heliscope sequencing, single molecule real time (SMRT) sequencing, nanopore sequencing, hybridization, mass spectroscopy-based sequencing, Sanger sequencing, transmission electron microscopy sequencing, or quantum sequencing.

In an embodiment, the containment protocol is a Centers for Disease Control approved protocol.

In an aspect, the present invention provides a method of characterizing viability of one or more microorganism populations, that includes the steps of: obtaining a sample at a location including one or more microorganism populations at one or more time points; determining a DNA sequence of one or more genomic DNA regions from the one or more microorganism populations at each of the one or more time points; identifying genetic variation at the one or more genomic DNA regions by comparing sequences of the one or more genomic DNA regions at each of the one or more time points and identifying nucleotides that differ from a reference and from other aligned reads, including association with a confidence score; determining, based on modeling the identified genetic variation, the viability of one or more microorganism populations whether one or more microorganism populations are evolving and hence viable; and implementing a containment protocol based on the viability assessment.

In an embodiment, the one or more microorganism populations are selected from the group consisting of bacteria, fungi, viruses, protozoans, and parasites.

In an embodiment, the bacteria are selected from the phylogenetic group consisting of Acidobacteria, Actinobacteria, Aquificae, Armatimonadetes, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermomicrobia, Thermotogae, and Verrucomicrobia.

In an embodiment, the bacteria are selected from the group consisting of *Actinomyces israelii, Bacillus anthracia, Bacillus cereus, Bacteroides fragilis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium tetani, Corynebacterium diphtheria, Ehrlichia canis, Ehrlichia chaffeensis, Enterococcus faecalis, Enterococcus faecium, Escherichia coli, Francisella tularensis, Haemophilus influenzae, Helicobacter pylori, Klebsiella pneumoniae, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Shigella dysenteriae, Staphylococcus aureus, Staphylococcus epidermidis, Staphylococcus saprophyticus, Streptococcus agalactiae, Streptococcus pneumoniae, Streptococcus pyogenes, Streptococcus viridans, Treponema pallidum, Ureaplasma urealyticum, Vibrio cholera, Yersinia pestis, Yersinia enterocolitica,* and *Yersinia pseudotuberculosis.*

In an embodiment, the virus are selected from the group consisting of Adenovirus, Herpes simplex, type 1, Herpes simplex, type 2, Varicella-zoster virus, Epstein-barn virus, Human cytomegalovirus, Human herpesvirus, type 8, Human papillomavirus, BK virus, JC virus, Smallpox, Hepatitis B virus, Parvovirus B19, Human astrovirus, Norwalk virus, coxsackievirus, hepatitis A virus, poliovirus, rhinovirus, Hepatitis C virus, yellow fever virus, dengue virus, West Nile virus, TBE virus, Rubella virus, Hepatitis E virus, Human immunodeficiency virus (HIV), Influenza virus, Lassa virus, Crimean-Congo hemorrhagic fever virus, Hantaan virus, Ebola virus, Marburg virus, Measles virus, Mumps virus, Parainfluenza virus, Respiratory syncytial virus, Rabies virus, Rotavirus, Orbivirus, Coltivirus, Banna virus, and zika virus.

In an embodiment, the fungi are selected from the group consisting of *Candida* species, *Candida albicans, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii, Pneumocystis carinii,* and *Stachybotrys chartarum.*

In an embodiment, the protozoa are selected from the group consisting of *Entamoeba histolytica, Entamoeba coli, Entamoeba dispar, Entamoeba moshkovskii, Entamoeba bangladeshi, Entamoeba hartmanni, Dientamoeba fragilis, Endolimax nana, Iodamoeba butschlii, Plasmodium malariae, Plasmodium falciparum, Plasmodium vivax, Plasmodium ovale, Naegleria fowleri, Acanthamoeba* species, *Balamuthia mandrillaris, Sappinia diploidea, Giardia lamblia, Giardia intestinalis, Giardia duodenalis, Toxoplasma gondii, Nippostrongylus brasiliensis, Cryptosporidium parvum, Cryptosporidium hominis, Cryptosporidium canis, Cryptosporidium felis, Cryptosporidium meleagridis, Cryptosporidium muris, Trichomonas vaginalis, Trypanosoma cruzi, Leishmania major, Leishmania tropica, Leishmania barziliensis, Leishmania mexicana, Leishmania guyanesis, Leishmania panamensis,* and *Trypanosoma brucei.*

In an embodiment, the DNA sequence of a plurality of genomic DNA fragments is obtained by massively parallel signature sequencing, Polony sequencing, 454 pyrosequencing, Illumina sequencing, SOLiD sequencing, ion semiconductor sequencing, DNA nanoball sequencing, heliscope sequencing, single molecule real time (SMRT) sequencing, nanopore sequencing, hybridization, mass spectroscopy-based sequencing, Sanger sequencing, transmission electron microscopy sequencing, or quantum sequencing.

In an embodiment, the containment protocol is a Centers for Disease Control approved protocol.

In an embodiment, the genetic variation is selected from the group consisting of single nucleotide polymorphisms, deletions, and insertions.

In an embodiment, the one or more genomic DNA regions are randomly selected or specifically targeted loci.

In an embodiment, the method further includes the steps of: determining that the genetic variation at a specific location within the one or more genomic DNA regions is in synonymous or non-synonymous sites, wherein a preponderance of non-synonymous variation indicates evolution and therefore viability of the one or more microorganism populations.

In an embodiment, the method further includes the steps of: analyzing, by site frequency spectrum analysis, the genetic variation at one or more genomic DNA regions at one or more time points; and determining, based on absence from an early time point and presence at a later time point, if that region experienced a reduction or elimination of variation among nucleotides near a mutation site (selective sweep), thereby indicating evolution by positive selection and therefore viability of the one or more microorganism populations.

In an embodiment, the genetic variation is modeled by Tajima's D statistical method.

In an embodiment, the method further includes the step of: modeling the accumulation of SNPs between multiple time points to estimate the probability that a population is evolving and hence viable.

In an embodiment, the method further includes the steps of: comparing sequence data at a locus or loci from two time points; and comparing the genetic variation between the two time points to determine if differentiation or evolution occurred as estimated by fixation index ($F_{ST}$, application of the Wright's F-statistic) to indicate potential viability of the one or more microorganism populations.

In an embodiment, the method further includes the steps of: using multiple population genetic estimates in a model to differentiate between different modes of evolution (i.e. drift, selection, migration, and mutation) to estimate the likelihood of evolution by natural selection and hence viability of a microbial population.

In an embodiment, the method further includes the steps of: modeling genetic variation at specific functional loci (including antimicrobial resistance loci) to determine if functional loci are evolving in order to provide additional support for viability and determine whether one or more environmental factors are exerting a selective pressure on these loci; and implementing a modified protocol based on this assessment.

In an embodiment, the method further includes the steps of: using algorithms to differentiate between sequencing error as well as demographic versus selection signals to estimate the likelihood of evolution by natural selection and hence viability of a microbial population.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

By "alteration" is meant an increase or decrease. An alteration may be by as little as 1%, 2%, 3%, 4%, 5%, 10%, 20%, 30%, or by 40%, 50%, 60%, or even by as much as 75%, 80%, 90%, or 100%. An alteration may be a change in sequence relative to a reference sequence or sequence of sample collected at a different time point or a change in expression level, activity, or epigenetic marker.

By "ameliorate" is meant decrease, suppress, attenuate, diminish, arrest, or stabilize the development or progression of a disease.

By "analog" is meant a molecule that is not identical, but has analogous functional or structural features.

By "biologic sample" is meant any tissue, cell, fluid, or other material derived from an organism or collected from the environment.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "control" is meant a standard or reference condition.

"Detect" refers to identifying the presence, absence or amount of the analyte to be detected.

By "diagnostic" is meant any method that identifies the presence of a pathologic condition or agent or characterizes the nature of a pathologic condition (e.g., an infection). Diagnostic methods differ in their sensitivity and specificity. While a particular diagnostic method may not provide a definitive diagnosis of a condition, it suffices if the method provides a positive indication that aids in diagnosis.

The phrase "in combination with" is intended to refer to all forms of administration that provide an agent, or the methods of the instant invention together with a second agent, such as an antiviral agent, or antibiotic agent, or an antifungal agent, where the two are administered concurrently or sequentially in any order.

The phrase "combination" embraces groups of compounds or non-drug therapies useful as part of a combination therapy. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner Substantially simultaneous administration can be accomplished, for example, by administering to the subject a single capsule having a fixed ratio of each therapeutic agent or in multiple, single capsules for each of the therapeutic agents.

The term "agent" as used herein is meant to refer to a polypeptide, polynucleotide, or fragment, or analog thereof, small molecule, inhibitory RNA, or other biologically active molecule.

The term "epigenetic marker" or "epigenetic change" as used herein is meant to refer to a change in the DNA sequences or gene expression by a process or processes that do not change the DNA coding sequence itself. In an exemplary embodiment, methylation is an epigenetic marker.

By "disease" is meant any condition or disorder that damages or interferes with the normal function of a cell, tissue, or organ.

By "effective amount" is meant the amount required to ameliorate the symptoms of a disease (e.g., a microbial infection) relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fluorescent detection" is meant the measurement of the signal of a labeled moiety of at least one of the one or more nucleotides or nucleotide analogs. Sequencing using fluorescent nucleotides typically involves photobleaching the fluorescent label after detecting an added nucleotide. In some embodiments, fluorescent detection can include bead-based fluorescent, FRET, infrared labels, pyrophosphatase, ligase methods including labeled nucleotides or polymerase or use of cyclic reversible terminators. In some embodiments, fluorescent detection can include direct methods of nanopores or optical waveguide including immobilized single molecules or in solution. Photobleaching methods include a reduced signal intensity, which builds with each addition of a fluorescently labeled nucleotide to the primer strand. By reducing the signal intensity, longer DNA templates are optionally sequenced.

By "fragment" is meant a portion of a polypeptide or nucleic acid molecule. This portion contains, at least 1%, 5%, 10%, 20%, 30%, 40%, 50%, 60%, 70%, 80%, or 90% of the entire length of the reference nucleic acid molecule or polypeptide. A fragment may contain 5, 10, 20, 30, 40, 50, 60, 70, 80, 90, or 100, 200, 300, 400, 500, 600, 700, 800, 900, 1000 or more nucleotides or amino acids. In some embodiments, a fragment may contain less than 1% of the entire length of the reference nucleic acid molecule or polypeptide. A fragment may contain 150 base pairs (bps) of nucleic acid molecule.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "sensitivity" is meant the percentage of subjects with a particular disease that are correctly detected as having the disease. For example, an assay that detects 98/100 of infections has 98% sensitivity.

The phrase "nucleic acid" as used herein refers to an oligonucleotide, nucleotide, polynucleotide, or to a fragment of any of these, to DNA or RNA of genomic or synthetic origin which may be single-stranded or double-stranded and may represent a sense or antisense strand, peptide nucleic acid (PNA), or to any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency (see e.g., Wahl, G. M. and S. L. Berger (1987) Methods Enzymol. 152:399; Kimmel, A. R. (1987) Methods Enzymol. 152:507). For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art. For most applications, washing steps that follow hybridization will also vary in stringency. Wash stringency conditions can be defined by salt concentration and by temperature.

As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

The term "gene" refers to a segment of deoxyribonucleic acid that encodes a polypeptide including the upstream and downstream regulatory sequences. Specifically, the term gene includes the promoter region upstream of the gene.

The term "promoter" or "promoter region" refers to a minimal sequence sufficient to direct transcription or to render promoter-dependent gene expression that is controllable for cell-type specific or tissue-specific gene expression, or is inducible by external signals or agents. Promoters may be located in the 5' or 3' regions of the gene. Promoter regions, in whole or in part, of a number of nucleic acids can be examined for sites of variation and/or mutation. In general, a promoter includes, at least, 50, 75, 100, 125, 150, 175, 200, 250, 300, 400, 500, 750, 1000, 1500, or 2000 nucleotides upstream of a given coding sequence (e.g., upstream of the coding sequence for genes). One of skill in the art will appreciate that a promoter location may vary outside these parameters for some genes, and also that some genes may comprise more than one promoter (e.g., multiple tissue specific promoters).

The term "sample" as used herein refers to any biological or chemical mixture for use in the method of the invention. The sample can be a biological sample. The sample can be collected from the surface of an environment (hospital, office building, building, shopping center, park, restaurant, plaza, mall, or public space) or individual.

By "marker" is meant any protein or polynucleotide having an alteration in expression level or activity that is associated with a disease or disorder. A marker may also mean a variant DNA or RNA sequence that has shown to contribute toward a disease or disorder.

By "mutation" is meant a DNA sequence found in the microbial sample that is not found in the corresponding DNA of that same microorganism in other samples. "Mutation" may also refer to patterns in the sequence of RNA from a sample that are not attributable to expected variations based on known information for an individual gene and are reasonably considered to be novel variations in, for example, the splicing pattern of one or more genes that has been specifically altered in the microbial cells of the sample.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" as recited herein may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH2)n—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the pooled tumor specific neo-antigens provided herein, including those listed by Remington's Pharmaceutical Sciences, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "single-nucleotide polymorphism/simple nucleotide polymorphism" (or "SNP") is meant a variation in a single nucleotide which may occur at some specific position in the genome, where each variation is present to some degree within a population (e.g., >1%).

The term "subject" as used herein is meant to include vertebrates, preferably a mammal. Mammals include, but are not limited to, humans, camels, horses, goats, sheep, cows, dogs, cats, and the like.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or a combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

Figure 1:
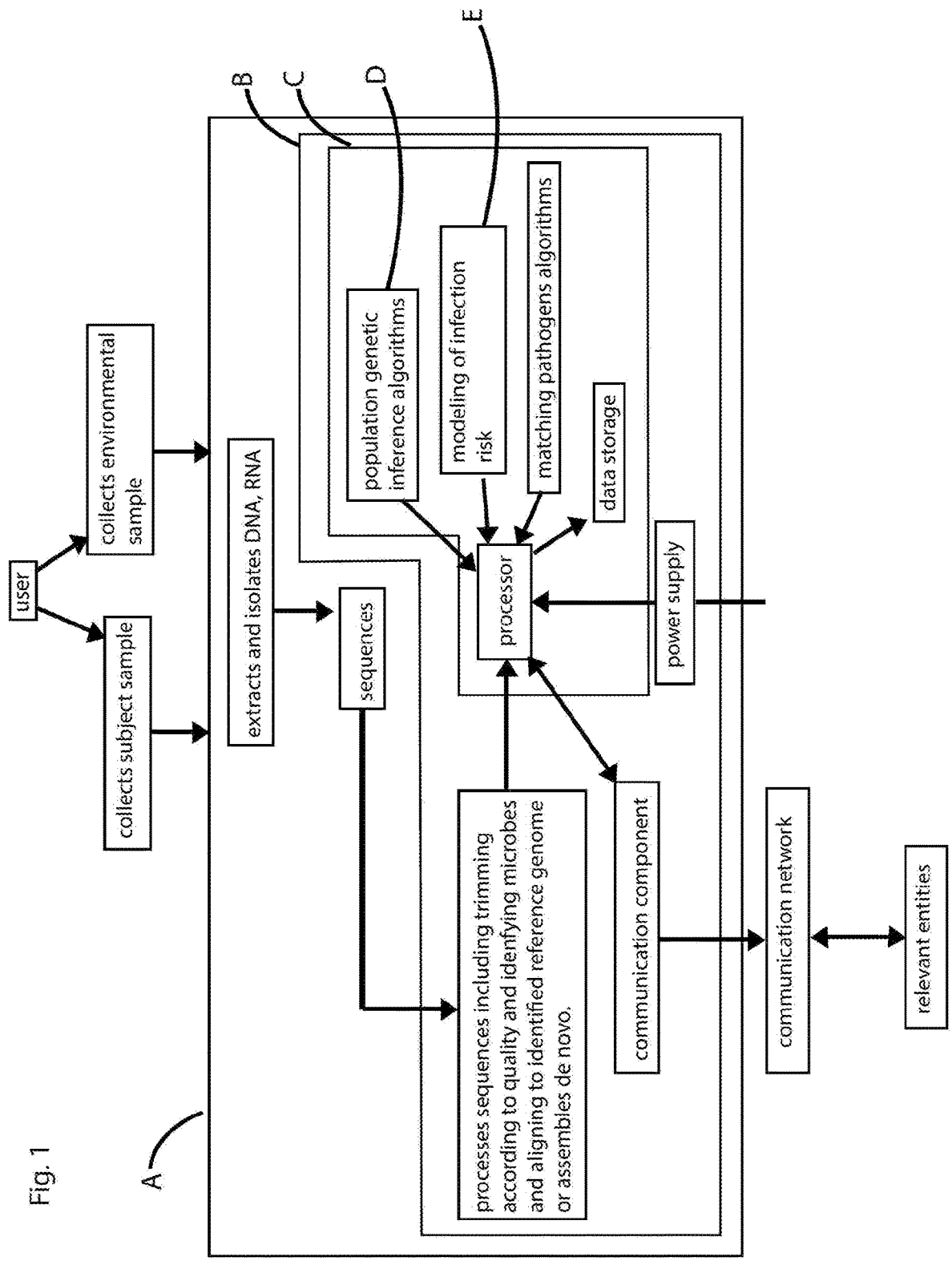
FIG. 1 is an illustration of the system which may be used for characterization of viability and infection risk of microbial populations with potential embodiments as a device (A), a system (B), and/or a software (C).
Figure 2:
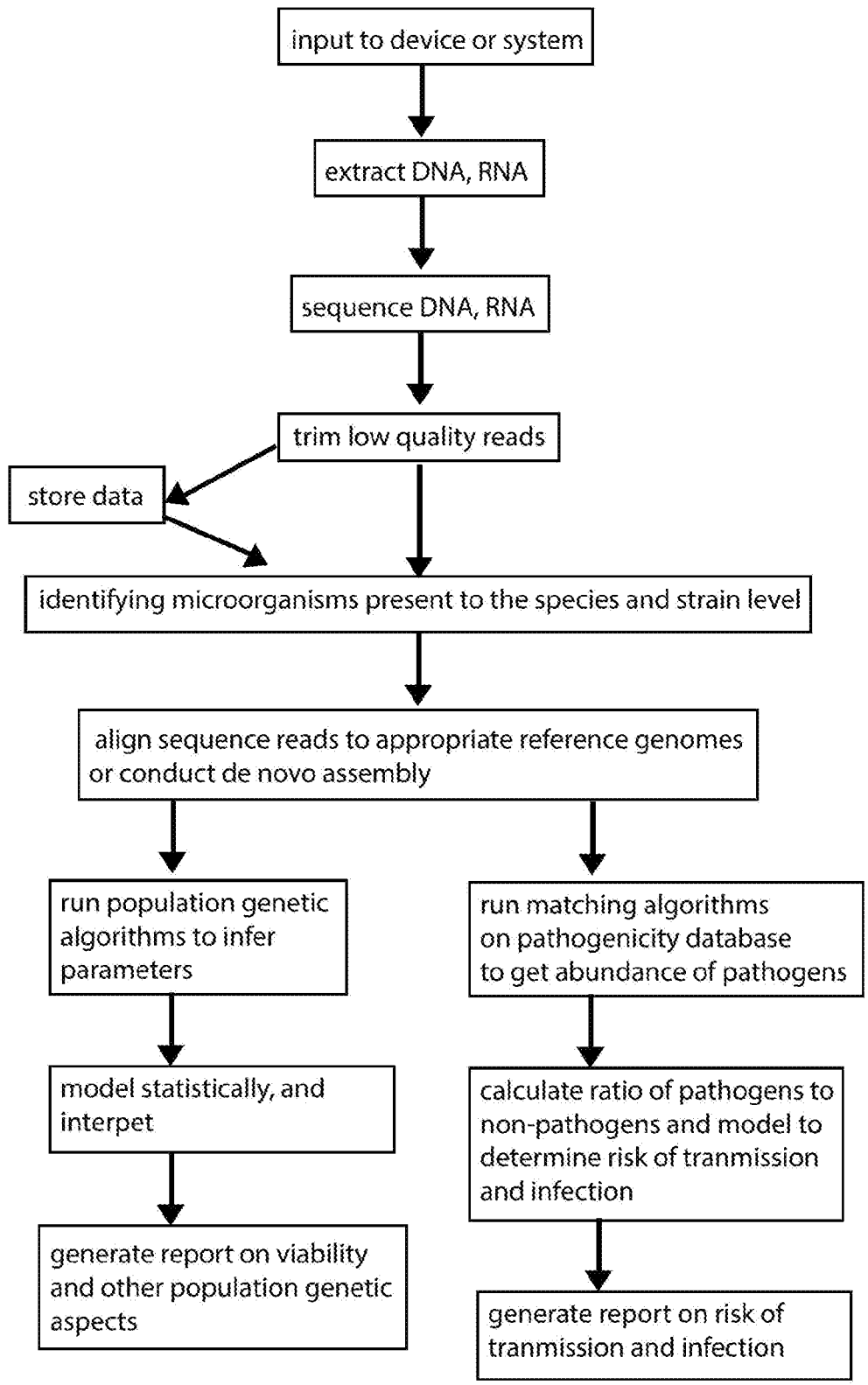
FIG. 2 is a flow chart illustrating the process of operation of the system of FIG. 1.

The present invention features methods for characterizing the viability of microbes within the environment and determining their risk of infection. The present invention features methods of characterizing DNA sequence data by calculating population genetic estimates, sometimes at multiple time points, to determine viability, as well as comparison of identified microbes to genomic and pathogenicity databases to calculate the ratio of pathogenic versus non-pathogenic strains to model risk of infection.

This invention relates to systems and methods for characterizing the viability of microorganisms, as well as the risk of infection from pathogens transmitted from surfaces. This refers to characterization of either single or mixed-microorganismal samples collected, and may include culturing mixed-microorganismal samples before sequencing in order to isolate a single species. These systems and methods include calculation of population genetic estimates, including utilizing measures of genetic variance at specific loci (including important functional and antibiotic resistant loci) and genome-wide. This may include analyzing metagenonomic sequence data and comparing at multiple time points to determine if a population is evolving, which would indicate (depending on the mechanism of evolution) that it is viable (i.e., alive). Additionally, these systems and methods will characterize the risk of transmission and infection by utilizing sequence data identified to the strain level (by available technology) and comparing these data to a pathogen database to model risk based on the ratio of pathogenic to non-pathogenic species and/or strains and infection rates. This model will be trained using machine learning as data is collected. This characterization of viability and risk of infection could be useful in many applications, such as in hospitals where such technology could allow hospitals to appropriately adjust cleaning approaches in an informed manner, and could help guide additional prevention strategies and/or empiric antimicrobial therapy.

Current approaches to characterize microbial populations, including viability and risk of infection from the environment, require specific assays that are time consuming and expensive. Laboratory culturing remains the gold standard to identify and characterize microbial populations. However, this approach takes upwards of ~3 days, depending on the growth rate of the specific bacterial species. It is also costly, and it can only characterize microbes which can be cultured. Recently, progress has been made in identification of microbes using next generation sequencing through comparison of metagenomic fragments to genomic databases, however, technology has not been developed which allows us to characterize viability and risk of infection from these populations solely by using these sequence data. Since current environmental testing technologies are unwieldy, environmental testing is often limited, even though the environment has been known to act as a reservoir for many pathogens.

For example, hospital acquired infections (HAIs) are a common cause of morbidity and mortality in the US. One in 25 people who check into a hospital get an infection and 1 in 9 of these patients die from that infection. This makes hospital acquired infections a leading cause of death in the US and an estimated 10 billion in direct costs is spent on this problem. Studies have shown that hospitals can prevent between 20 and 70% of HAIs by modifying hospital practices, such as implementing cleaning practices that appropriately target pathogens. Even though an increasing number of studies are showing that the hospital environment is acting as a significant reservoir for these pathogens, environmental testing is severely limited. This means that hospitals are cleaning blindly, and waiting until patients get sick to process samples and identify pathogens. This is because their current environmental testing tools, including ATP testing and culturing are slow, labor intensive, and costly. DNA based tools have been developed to identify microbes, include PCR based approaches and high throughput sequencing and analysis pipelines. However, these approaches have primarily focused on patient samples instead of the environment. Furthermore, most tools developed to test the environment identify and quantify the amount of pathogen present, but do not characterize whether those organisms are alive or dead, or assess the risk of infection for the patient. There is a pressing need for technology which can not only rapidly identify microbes in the environment, but can also determine if those microbes are pathogenic, viable (alive), and pose a risk.

An additional concern of grave importance is the ability of some populations of bacteria to survive treatment of one or multiple antibiotic treatments. The overuse of antibiotics has led to an increase in these antibiotic or multi-drug resistant bacteria which has become a major public health concern. In the case of hospitals, patients are widely monitored for incidence of antibiotic resistant infection, but the environment is rarely monitored. Instead once patients get sick, samples are taken to be analyzed in different ways, such as by culturing and exposing to antibiotics to determine if bacteria survive, or by amplification and sequencing of known antibiotic associated loci. There is a great need to develop affordable and rapid methods to characterize antibiotic resistance from the environment, before patients get sick.

Population genetic estimates could allow us to characterize populations based on DNA sequence for regions of the genome which have sufficient sequencing coverage, including determining if populations are evolving, expanding, contracting and or migrating. It is now possible to differentiate between evolutionary shifts and demography (e.g. differentiation versus population contraction) based on sequence data. For example, the use of Bayesian models on next-generation population genomic data have revealed possibilities of differentiating between demographic and evolutionary signatures, and show promise for pinpointing regions of genomes which are under selection. Additionally, ecological models have been developed which allow us to understand competition in a more nuanced manner. Studies have found that an important factor moderating infection is not only presence of a pathogen but whether competing strains/species are present in a sample. This dynamic explains why treating patients who suffer from *Clostridium difficile* infection (CDI) with non-pathogenic strains of *C. difficile* is highly effective. However, development of a technology which applies these principles to characterize high risk environments has been lacking.

In addition to the hospital, there are many high risk environments in which such technology could be useful. For example, in the case of bio-terrorist attacks, food borne disease outbreaks, and epidemics, the ability to use nucleotide sequence data to not only identify microbial populations but characterize these populations to determine viability and risk of infection could be of vital importance to those dealing in immigration, homeland security, food safety and infection control.

With the impressive ongoing advances in sequencing technology including the ability to rapidly and affordably sequence environmentally collected samples to a depth which allows for population genetic characterization and coverage of virulence makers and the ability to re-sequence specific molecular targets to increase coverage, it is necessary to develop new technology which goes beyond identification and further characterizes these populations.

Hospital Acquired Infections

Hospital-acquired infection (HAI)—also known as nosocomial infection—is an infection that is contracted by a patient while they are under medical care. It can be spread in the hospital environment, nursing home environment, rehabilitation facility, clinic, or other clinical settings. Infection is spread to the susceptible patient in the clinical setting by a number of means. Health care staff can spread infection, in addition to contaminated equipment, surfaces, bed linens, or air droplets. The infection can originate from the outside environment, another infected patient, staff that may be infected, or in some cases, the source of the infection cannot be determined. In some cases the microorganism originates from the patient's own microbiota, becoming opportunistic after surgery or other procedures that compromise the protective skin barrier or the immune system. Though the patient may have contracted the infection from their own body, the infection is still considered nosocomial since it develops in the health care setting.

In the United States, the Centers for Disease Control and Prevention estimated roughly 1.7 million hospital-associated infections, from all types of microorganisms, including bacteria and fungi combined, cause or contribute to 99,000 deaths each year. In Europe, where hospital surveys have been conducted, the category of gram-negative infections are estimated to account for two-thirds of the 25,000 deaths each year. Nosocomial infections can cause severe pneumonia and infections of the urinary tract, bloodstream and other parts of the body. Many types are difficult to treat with antibiotics, and in addition, antibiotic resistance can complicate treatment.

Organisms commonly associated with HAI include, but are not limited to *Staphylococcus aureus*, Methicillin resistant *Staphylococcus aureus* (MRSA), *Candida albicans, Pseudomonas aeruginosa, Acinetobacter baumannii, Stenotrophomonas maltophilia, Clostridium difficile, Escherichia coli, Tuberculosis*, Vancomycin-resistant *Enterococcus*, and Legionnaires' disease.

Micro-organisms are known to survive on inanimate 'touch' surfaces for extended periods of time. This can be especially troublesome in hospital environments where patients with immunodeficiencies are at enhanced risk for contracting nosocomial infections.

High touch surfaces commonly found in hospital rooms, such as bed rails, call buttons, touch plates, chairs, door handles, light switches, grab rails, intravenous poles, dispensers (alcohol gel, paper towel, soap), dressing trolleys, and counter and table tops are known to be contaminated with *Staphylococcus*, MRSA (one of the most virulent strains of antibiotic-resistant bacteria), vancomycin-resistant *Enterococcus* (VRE), and other nosocomial causing pathogens. For example, objects in closest proximity to patients have the highest levels of MRSA and VRE. This is why high touch surfaces in hospital rooms can serve as sources, or reservoirs, for the spread of bacteria from the hands of healthcare workers and visitors to patients.

Infectious Disease

Infection is the invasion of an organism's body tissues by disease-causing agents, their multiplication, and the reaction of host tissues to these organisms and the toxins they produce. Infectious disease, also known as transmissible disease or communicable disease, is illness resulting from an infection. Infections are caused by infectious agents including viruses, viroids, prions, bacteria, nematodes such as parasitic roundworms and pinworms, arthropods such as ticks, mites, fleas, and lice, fungi such as ringworm, and other macroparasites such as tapeworms and other helminths. Hosts can fight infections using their immune system. Mammalian hosts react to infections with an innate response, often involving inflammation, followed by an adaptive response. Specific medications used to treat infections include antibiotics, antivirals, antifungals, antiprotozoals, and antihelminthics. Infectious diseases resulted in 9.2 million deaths in 2013 (about 17% of all deaths).

Among the vast varieties of microorganisms, relatively few cause disease in otherwise healthy individuals. Infectious disease results from the interplay between those few pathogens and the defenses of the hosts they infect. The appearance and severity of disease resulting from any pathogen, depends upon the ability of that pathogen to damage the host as well as the ability of the host to resist the pathogen. However, a host's immune system can also cause damage to the host itself in an attempt to control the infection. Clinicians therefore classify infectious microorganisms or microbes according to the status of host defenses—either as primary pathogens or as opportunistic pathogens:

Primary pathogens cause disease as a result of their presence or activity within the normal, healthy host, and their intrinsic virulence (the severity of the disease they cause) is, in part, a necessary consequence of their need to reproduce and spread. Many of the most common primary pathogens of humans only infect humans, however many serious diseases are caused by organisms acquired from the environment or that infect non-human hosts.

Opportunistic pathogens can cause an infectious disease in a host with depressed resistance. Opportunistic infection may be caused by microbes ordinarily in contact with the host, such as pathogenic bacteria or fungi in the gastrointestinal or the upper respiratory tract, and they may also result from (otherwise innocuous) microbes acquired from other hosts (as in *Clostridium difficile* colitis) or from the environment as a result of traumatic introduction (as in surgical wound infections or compound fractures). An opportunistic disease requires impairment of host defenses, which may occur as a result of genetic defects (such as Chronic granulomatous disease), exposure to antimicrobial drugs or immunosuppressive chemicals (as might occur following poisoning or cancer chemotherapy), exposure to ionizing radiation, or as a result of an infectious disease with immunosuppressive activity (such as with measles, malaria or HIV disease). Primary pathogens may also cause more severe disease in a host with depressed resistance than would normally occur in an immune-sufficient host.

For infecting organisms to survive and repeat the infection cycle in other hosts, they (or their progeny) must leave an existing reservoir and cause infection elsewhere. Infection transmission can take place via many potential routes. Droplet contact, also known as the respiratory route, and the resultant infection can be termed airborne disease. If an infected person coughs or sneezes on another person the microorganisms, suspended in warm, moist droplets, may enter the body through the nose, mouth or eye surfaces. Fecal-oral transmission is defined by foodstuffs or water becoming contaminated (by people not washing their hands before preparing food, or untreated sewage being released into a drinking water supply) and the people who eat and drink them become infected. Common fecal-oral transmitted pathogens include *Vibrio cholerae, Giardia* species, rotaviruses, *Entameba histolytica, Escherichia coli*, and tape worms. Most of these pathogens cause gastroenteritis. Sexual transmission, with the resulting disease being called sexually transmitted disease, is another route. Oral transmission includes diseases that are transmitted primarily by oral means may be caught through direct oral contact such as kissing, or by indirect contact such as by sharing a drinking glass or a cigarette. Transmission may also be by direct contact. Some diseases that are transmissible by direct contact include athlete's foot, impetigo and warts. Vertical transmission requires direct contact from the mother to an embryo, fetus or baby during pregnancy or childbirth. It can occur when the mother gets an infection as an intercurrent disease in pregnancy. Iatrogenic transmission is due to medical procedures such as injection or transplantation of infected material.

Virulence

Virulence is the degree of pathogenicity within a group or species of parasites as indicated by case fatality rates and/or the ability of the organism to invade the tissues of the host. The pathogenicity of an organism—its ability to cause disease—is determined by its virulence factors. Virulence can describe either disease severity or a pathogen's infectivity.

In an ecological context, virulence can be defined as the host's parasite-induced loss of fitness. Virulence can be understood in terms of proximate causes—those specific traits of the pathogen that help make the host ill—and ultimate causes—the evolutionary pressures that lead to virulent traits occurring in a pathogen strain.

The ability of bacteria to cause disease is described in terms of the number of infecting bacteria, the route of entry into the body, the effects of host defense mechanisms, and intrinsic characteristics of the bacteria called virulence factors. Many virulence factors are so-called effector proteins that are injected into the host cells by special secretion machines such as the type 3 secretion system. Host-mediated pathogenesis is often important because the host can respond aggressively to infection with the result that host defense mechanisms do damage to host tissues while the infection is being countered.

The virulence factors of bacteria are typically proteins or other molecules that are synthesized by enzymes. These proteins are coded for by genes in chromosomal DNA, bacteriophage DNA or plasmids. Certain bacteria employ mobile genetic elements and horizontal gene transfer. Therefore, strategies to combat certain bacterial infections by targeting these specific virulence factors and mobile genetic elements have been proposed. Bacteria use quorum sensing to synchronize release of the molecules. These are all proximate causes of morbidity in the host.

Pathogenicity

In biology, a pathogen in the oldest and broadest sense is anything that can produce disease, a term which came into use in the 1880s. Typically the term is used to describe an infectious agent such as a virus, bacterium, prion, fungus, viroid, or parasite that causes disease in its host. The host may be a human, an animal, a plant, a fungus, or even another micro-organism.

There are several substrates including pathways where the pathogens can invade a host. The principal pathways have different episodic time frames, but soil contamination has the longest or most persistent potential for harboring a pathogen. Diseases caused by organisms in humans are known as pathogenic diseases.

Pathogenicity is the potential disease-causing capacity of pathogens. Pathogenicity is related to virulence in meaning, but some authorities have come to distinguish it as a qualitative term, whereas the latter is quantitative. By this standard, an organism may be said to be pathogenic or non-pathogenic in a particular context, but not "more pathogenic" than another. Such comparisons are described instead in terms of relative virulence. Pathogenicity is also distinct from the transmissibility of the virus, which quantifies the risk of infection. A pathogen may be described in terms of its ability to produce toxins, enter tissue, colonize, hijack nutrients, and its ability to immunosuppress the host.

Sequencing Methods

In some embodiments, the present invention is based on employing one or more sequencing methods to characterize micro-organismal populations and determine their viability and risk of causing infection. A number of sequencing technologies, such as Next Generation Sequencing, may be used.

Multiple, fragmented sequence reads must be assembled together on the basis of their overlapping areas. Next-generation sequencing applies to genome sequencing, genome resequencing, transcriptome profiling (RNA-Seq), DNA-protein interactions (ChIP-sequencing), and epigenome characterization. Resequencing is necessary, because the genome of a single individual of a species will not indicate all of the genome variations among other individuals of the same species. The high demand for low-cost sequencing has driven the development of high-throughput sequencing (or next-generation sequencing) technologies that parallelize the sequencing process, producing thousands or millions of sequences concurrently. High-throughput sequencing technologies are intended to lower the cost of DNA sequencing beyond what is possible with standard dye-terminator methods. In ultra-high-throughput sequencing as many as 500,000 sequencing-by-synthesis operations may be run in parallel.

The first of the next-generation sequencing technologies, massively parallel signature sequencing (or MPSS), is a bead-based method that uses a complex approach of adapter ligation followed by adapter decoding, reading the sequence in increments of four nucleotides. This method makes it susceptible to sequence-specific bias or loss of specific sequences. The essential properties of the MPSS output are typical of later "next-generation" data types, including hundreds of thousands of short DNA sequences. In the case of MPSS, these are typically used for sequencing cDNA for measurements of gene expression levels.

The Polony sequencing method was among the first next-generation sequencing systems and was used to sequence a full *E. coli* genome in 2005. It combined an in vitro paired-tag library with emulsion PCR, an automated microscope, and ligation-based sequencing chemistry to sequence an *E. coli* genome at an accuracy of >99.9999% and a cost approximately 1/9 that of Sanger sequencing.

The 454 pyrosequencing method amplifies DNA inside water droplets in an oil solution (emulsion PCR), with each droplet containing a single DNA template attached to a single primer-coated bead that then forms a clonal colony. The sequencing machine contains many picoliter-volume wells each containing a single bead and sequencing enzymes. Pyrosequencing uses luciferase to generate light for detection of the individual nucleotides added to the nascent DNA, and the combined data are used to generate sequence read-outs.

Illumina (Solexa) sequencing involves a sequencing method based on reversible dye-terminators technology, and engineered polymerases. It is based on "DNA Clusters" or "DNA colonies", which involves the clonal amplification of DNA on a surface. In this method, DNA molecules and primers are first attached on a slide or flow cell and amplified with polymerase so that local clonal DNA colonies, later coined "DNA clusters", are formed. To determine the sequence, four types of reversible terminator bases (RT-bases) are added and non-incorporated nucleotides are washed away. A camera takes images of the fluorescently labeled nucleotides. Then the dye, along with the terminal 3' blocker, is chemically removed from the DNA, allowing for the next cycle to begin. Unlike pyrosequencing, the DNA chains are extended one nucleotide at a time and image acquisition can be performed at a delayed moment, allowing for very large arrays of DNA colonies to be captured by sequential images taken from a single camera.

Decoupling the enzymatic reaction and the image capture allows for optimal throughput and theoretically unlimited sequencing capacity. With an optimal configuration, the ultimately reachable instrument throughput is thus dictated solely by the analog-to-digital conversion rate of the camera, multiplied by the number of cameras and divided by the number of pixels per DNA colony required for visualizing them optimally (approximately 10 pixels/colony). In 2012, with cameras operating at more than 10 MHz A/D conversion rates and available optics, fluidics and enzymatics, throughput can be multiples of 1 million nucleotides/second, corresponding roughly to 1 human genome equivalent at 1× coverage per hour per instrument, and 1 human genome re-sequenced (at approx. 30×) per day per instrument (equipped with a single camera).

SOLiD sequencing technology employs sequencing by ligation. Here, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting beads, each containing single copies of the same DNA molecule, are deposited on a glass slide. The result is sequences of quantities and lengths comparable to Illumina sequencing. This sequencing by ligation method has been reported to have some issue sequencing palindromic sequences.

Ion semiconductor sequencing uses standard sequencing chemistry, but with a novel, semiconductor based detection system. This method of sequencing is based on the detection of hydrogen ions that are released during the polymerisation of DNA, as opposed to the optical methods used in other sequencing systems. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogens and a proportionally higher electronic signal.

DNA nanoball sequencing is a type of high throughput sequencing technology used to determine the entire genomic sequence of an organism. The company Complete Genomics uses this technology to sequence samples submitted by independent researchers. The method uses rolling circle replication to amplify small fragments of genomic DNA into DNA nanoballs. Unchained sequencing by ligation is then used to determine the nucleotide sequence. This method of DNA sequencing allows large numbers of DNA nanoballs to be sequenced per run and at low reagent costs compared to other next generation sequencing platforms. However, only short sequences of DNA are determined from each DNA nanoball which makes mapping the short reads to a reference genome difficult. This technology has been used for multiple genome sequencing projects and is scheduled to be used for more.

Heliscope sequencing is a method of single-molecule sequencing that uses DNA fragments with added poly-A tail adapters which are attached to the flow cell surface. The next steps involve extension-based sequencing with cyclic washes of the flow cell with fluorescently labeled nucleotides (one nucleotide type at a time, as with the Sanger method). The reads are performed by the Heliscope sequencer. The reads are short, averaging 35 bp.

Single molecule real time sequencing (SMRT sequencing) is based on the sequencing by synthesis approach. The DNA is synthesized in zero-mode wave-guides (ZMWs)—small well-like containers with the capturing tools located at the bottom of the well. The sequencing is performed with use of unmodified polymerase (attached to the ZMW bottom) and fluorescently labelled nucleotides flowing freely in the solution. The wells are constructed in a way that only the fluorescence occurring by the bottom of the well is detected. The fluorescent label is detached from the nucleotide upon its incorporation into the DNA strand, leaving an unmodified DNA strand. According to Pacific Biosciences (PacBio), the SMRT technology developer, this methodology allows detection of nucleotide modifications (such as cytosine methylation). This happens through the observation of polymerase kinetics. This approach allows reads of 20,000 nucleotides or more, with average read lengths of 5 kilobases. In 2015, Pacific Biosciences announced the launch of a new sequencing instrument called the Sequel System, with 1 million ZMWs compared to 150,000 ZMWs in the PacBio RS II instrument.

DNA sequencing methods currently under development include reading the sequence as a DNA strand transits through nanopores, and microscopy-based techniques, such as atomic force microscopy or transmission electron microscopy that are used to identify the positions of individual nucleotides within long DNA fragments (>5,000 bp) by nucleotide labeling with heavier elements (e.g., halogens) for visual detection and recording. Third generation technologies aim to increase throughput and decrease the time to result and cost by eliminating the need for excessive reagents and harnessing the processivity of DNA polymerase.

Nanopore sequencing is based on the readout of electrical signals occurring at nucleotides passing by alpha-hemolysin pores covalently bound with cyclodextrin. The DNA passing through the nanopore changes its ion current. This change is dependent on the shape, size and length of the DNA sequence. Each type of the nucleotide blocks the ion flow through the pore for a different period of time. The method has a potential of development as it does not require modified nucleotides, however single nucleotide resolution is not yet available.

Two main areas of nanopore sequencing in development are solid state nanopore sequencing, and protein based nanopore sequencing. Protein nanopore sequencing utilizes membrane protein complexes $\alpha$-Hemolysin and MspA (*Mycobacterium* Smegmatis Porin A), which show great promise given their ability to distinguish between individual and groups of nucleotides. In contrast, solid-state nanopore sequencing utilizes synthetic materials such as silicon nitride and aluminum oxide and it is preferred for its superior mechanical ability and thermal and chemical stability. The fabrication method is essential for this type of sequencing given that the nanopore array can contain hundreds of pores with diameters smaller than eight nanometers.

The concept originated from the idea that single stranded DNA or RNA molecules can be electrophoretically driven in a strict linear sequence through a biological pore that can be less than eight nanometers, and can be detected given that the molecules release an ionic current while moving through the pore. The pore contains a detection region capable of recognizing different bases, with each base generating various time specific signals corresponding to the sequence of bases as they cross the pore which are then evaluated. When implementing this process it is important to note that precise control over the DNA transport through the pore is crucial for success. Various enzymes such as exonucleases and polymerases have been used to moderate this process by positioning them near the pore's entrance.

Another approach uses measurements of the electrical tunnelling currents across single-strand DNA as it moves through a channel Depending on its electronic structure, each base affects the tunnelling current differently, allowing differentiation between different bases. The use of tunnelling currents has the potential to sequence orders of magnitude faster than ionic current methods and the sequencing of several DNA oligomers and micro-RNA has already been achieved.

Sequencing by hybridization is a non-enzymatic method that uses a DNA microarray. A single pool of DNA whose sequence is to be determined is fluorescently labeled and hybridized to an array containing known sequences. Strong hybridization signals from a given spot on the array identifies its sequence in the DNA being sequenced.

This method of sequencing utilizes binding characteristics of a library of short single stranded DNA molecules (oligonucleotides), also called DNA probes, to reconstruct a target DNA sequence. Non-specific hybrids are removed by washing and the target DNA is eluted. Hybrids are re-arranged such that the DNA sequence can be reconstructed. The benefit of this sequencing type is its ability to capture a large number of targets with a homogenous coverage. A large number of chemicals and starting DNA is usually required. However, with the advent of solution-based hybridization, much less equipment and chemicals are necessary.

Mass spectrometry may be used to determine DNA sequences. Matrix-assisted laser desorption ionization time-of-flight mass spectrometry, or MALDI-TOF MS, has specifically been investigated as an alternative method to gel electrophoresis for visualizing DNA fragments. With this method, DNA fragments generated by chain-termination sequencing reactions are compared by mass rather than by size. The mass of each nucleotide is different from the others and this difference is detectable by mass spectrometry. Single-nucleotide mutations in a fragment can be more easily detected with MS than by gel electrophoresis alone. MALDI-TOF MS can more easily detect differences between RNA fragments, so researchers may indirectly sequence DNA with MS-based methods by converting it to RNA first.

The higher resolution of DNA fragments permitted by MS-based methods is of special interest to researchers in forensic science, as they may wish to find single-nucleotide polymorphisms in human DNA samples to identify individuals. These samples may be highly degraded so forensic researchers often prefer mitochondrial DNA for its higher stability and applications for lineage studies. MS-based sequencing methods have been used to compare the sequences of human mitochondrial DNA from samples in a Federal Bureau of Investigation database and from bones found in mass graves of World War I soldiers.

Early chain-termination and TOF MS methods demonstrated read lengths of up to 100 base pairs. Researchers have been unable to exceed this average read size; like chain-termination sequencing alone, MS-based DNA sequencing may not be suitable for large de novo sequencing projects. Even so, a recent study did use the short sequence reads and mass spectroscopy to compare single-nucleotide polymorphisms in pathogenic *Streptococcus* strains.

In microfluidic Sanger sequencing the entire thermocycling amplification of DNA fragments as well as their separation by electrophoresis is done on a single glass wafer (approximately 10 cm in diameter) thus reducing the reagent usage as well as cost. In some instances researchers have shown that they can increase the throughput of conventional sequencing through the use of microchips. Research will still need to be done in order to make this use of technology effective.

Transmission electron microscopy DNA sequencing directly visualizes the sequence of DNA molecules using electron microscopy. The first identification of DNA base pairs within intact DNA molecules by enzymatically incorporating modified bases, which contain atoms of increased atomic number, direct visualization and identification of individually labeled bases within a synthetic 3,272 base-pair DNA molecule and a 7,249 base-pair viral genome has been demonstrated.

The RNAP sequencing method is based on use of RNA polymerase (RNAP), which is attached to a polystyrene bead. One end of DNA to be sequenced is attached to another bead, with both beads being placed in optical traps. RNAP motion during transcription brings the beads in closer and their relative distance changes, which can then be recorded at a single nucleotide resolution. The sequence is deduced based on the four readouts with lowered concentrations of each of the four nucleotide types, similarly to the Sanger method. A comparison is made between regions and sequence information is deduced by comparing the known sequence regions to the unknown sequence regions.

Methods have been developed to analyze full sets of protein interactions using a combination of 454 pyrosequencing and an in vitro virus mRNA display method. Specifically, this method covalently links proteins of interest to the mRNAs encoding them, then detects the mRNA pieces using reverse transcription PCRs. The mRNA may then be amplified and sequenced. The combined method was titled In Vitro Virus High Throughput Sequencing (IVV-HiTSeq) and can be performed under cell-free conditions, though its results may not be representative of in vivo conditions.

The success of a DNA sequencing protocol is dependent on the sample preparation. A successful DNA extraction will yield a sample with long, non-degraded strands of DNA which require further preparation according to the sequencing technology to be used. For Sanger sequencing, either cloning procedures or PCR are required prior to sequencing. In the case of next generation sequencing methods, library preparation is required before processing.

With the advent of next generation sequencing, Illumina and Roche 454 methods have become a common approach to transcriptomic studies (RNAseq). RNA can be extracted from tissues of interest and converted to complimentary DNA (cDNA) using reverse transcriptase—a DNA polymerase that synthesizes a complimentary DNA based on existing strands of RNA in a PCR-like manner Complimentary DNA can be processed the same way as genomic DNA, allowing the expression levels of RNAs to be determined for the tissue selected.

This invention relates to systems and methods which describe a novel affordable and rapid approach to characterize microbes in single or mixed microbial populations by analyzing high throughput sequencing and/or targeted sequencing data using evolutionary and ecological genomics tools including population genetic estimates and statistical modeling. While methods exist for identification of microbes from single and mixed-microbial populations, the present invention relates to characterizing these populations in further useful ways including estimating viability and risk of infection. Methods described may characterize viability and infection risk by analyzing sequence data and comparing to a database which includes information on pathogenicity of strains in order to generate two reports: 1) a viability estimate (generated by calculating a number of population genetic estimates at multiple time points), and 2) a risk estimate (based on comparison to a database which contains data on the pathogenicity of strains of microbes, data collected on rates of infection, and statistical modeling). This invention may allow users to determine the viability and infection risk of microbes based on sequence data alone, without employing other approaches, such as culturing, which are time intensive and expensive.

In this invention, sequence data generated using different sequencing approaches, such as targeted panels (including phylogenetic, virulence, and antibiotic resistance markers) as well as whole genome or transcriptome sequencing, may be used. These data may be analyzed using available metagenomic tools to identify microbes present. These data may then be subjected to the system and methods disclosed herein including 1) calculation of population genetic estimates to analyze data collected at multiple time points to determine if populations are viable, and 2) analysis of ratios of commensal versus harmful microbial species and/or strains and modeling to determine the risk of infection. These analyses may be used separately and may also be integrated to determine risk of pathogens in the environment. These methods may involve using sequence data analyzed using a processor and memory by using computer instructions to execute specific analyses.

More specifically, for microorganisms in a sample for which there is sufficient sequence coverage and sequence uniqueness to differentiate from other microbes, the method to determine viability and risk may involve calculating population genetic parameters using complementary approaches, at specific loci or across the genome by using a sliding windowed analysis. Metrics calculated may include but may not be limited to nucleotide diversity ($\theta\pi$), genetic variance ($\theta_{Waterson}$), evidence of selection (Tajima's D), genetic differentiation by comparing specific loci or windows at multiple time points ($F_{ST}$) with early time points also used as an outgroup to model population expansion and evolution (e.g., identifying novel polymorphisms and the spread of such polymorphisms over time). Unbiased estimates may be implemented for pooled samples and to account for sequencing errors. Pool size may be estimated based on currently available tools to estimate abundance. Complementary estimates may be calculated to determine if there is evidence to indicate mechanisms of evolution at work including migration and natural selection, and to differentiate between selection and demographic signals. Loci of interest that show evidence of selection will be subjected to outlier analysis and the test estimate distribution will be compared to a null distribution to determine if it is significantly different from zero (see details below). Additionally, Bayesian models may be employed to analyze molecular variance and characterize population structure, and machine learning will be used to test big data sets to build a robust model to calculate transmission and infection risk from pathogens (see details below). These calculations may be computed on individual microbes or pooled populations of microbes (as found in metagenomic samples) and different algorithms may be used to calculate these alternative sample types. Populations which show evidence of selection (e.g., selective sweeps) that may be differentiated from demographic signatures are reported as having a higher probability of being viable.

For microorganisms in a sample which are able to be identified down to the subspecies level or which are identified to species level for species that are widely known to be pathogenic, comparisons may be made to a database which includes pathogenicity data to characterize the nature of microbes in said sample. Methods may also include calculating ratio of abundance of pathogenic versus non-pathogenic strains/species in order to statistically model infection risk. This builds on the concept that areas of low microbial abundance and diversity may be suitable for opportunistic pathogens to grow and establish both on surfaces and in the body and that beneficial bacteria may competitively inhibit or directly fight off pathogenic bacteria. This is one motivation for taking probiotics to treat bacterial infections such as *Clostridium difficile* infection (CDI).

Sequence data referred to in this invention may include, but is not limited to, RNA, DNA and protein sequence from a number of different organisms including fungi, bacteria, viruses, viroids, and parasites.

This invention may have many applications. For example, it may illuminate the microbial ecosystem on hospital surfaces and alert them to the presence of pathogens which are viable, and that have a high risk of infecting patients. This information will allow hospitals to clean in an appropriately targeted manner, using cleaning tools suited to the pathogens present. It also alerts the hospital to the presence of pathogens before patients get sick, and decrease the risk to patients.

This invention may also characterize antibiotic resistance in microbial populations. This may involve identifying antibiotic resistance loci based on a database and calculating population genetic estimates described above to explore whether antibiotic resistant genes are under selection or are evolving. In which case, cleaning procedures and disease treatment may be modified by the hospital or clinicians to relieve these selective pressures.

An additional potential embodiment of this invention is the comparison of sequences and markers to determine relatedness to microorganisms found in other local and distant areas, which could indicate avenues of transmission and spread of these pathogens and antibiotic resistance.

This invention is an improvement on current environmental testing tools because it is rapid (<24 hrs for results compared to the standard time of at least ~3 days for results), cheaper, and more effective (e.g., it will be able to characterize microbes that can't be cultured). An advantage of these new tools is that only DNA sequence data, and no other complementary assays (e.g., FACS or culturing), is required to determine viability and infection risk of a population.

Characterizing Viability and Risk

Included is the description of the embodiments of the systems and methods for characterizing the viability and risk of transmission and infection of microbial populations using sequence data. These systems and methods are described in more detail here and in reference to the figures.

Figure 3:
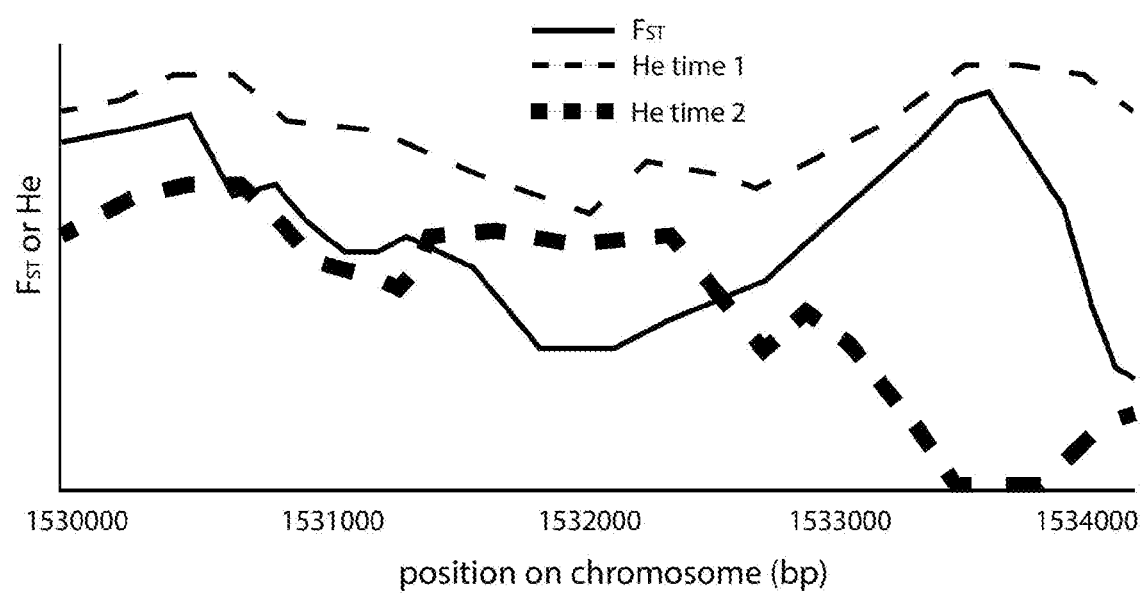
FIG. 3 is an illustrated example of results which may indicate selection at a specific locus in FIG. 1(C). These results are statistically modelled to estimate viability (see Detailed Description below).
Figure 4:
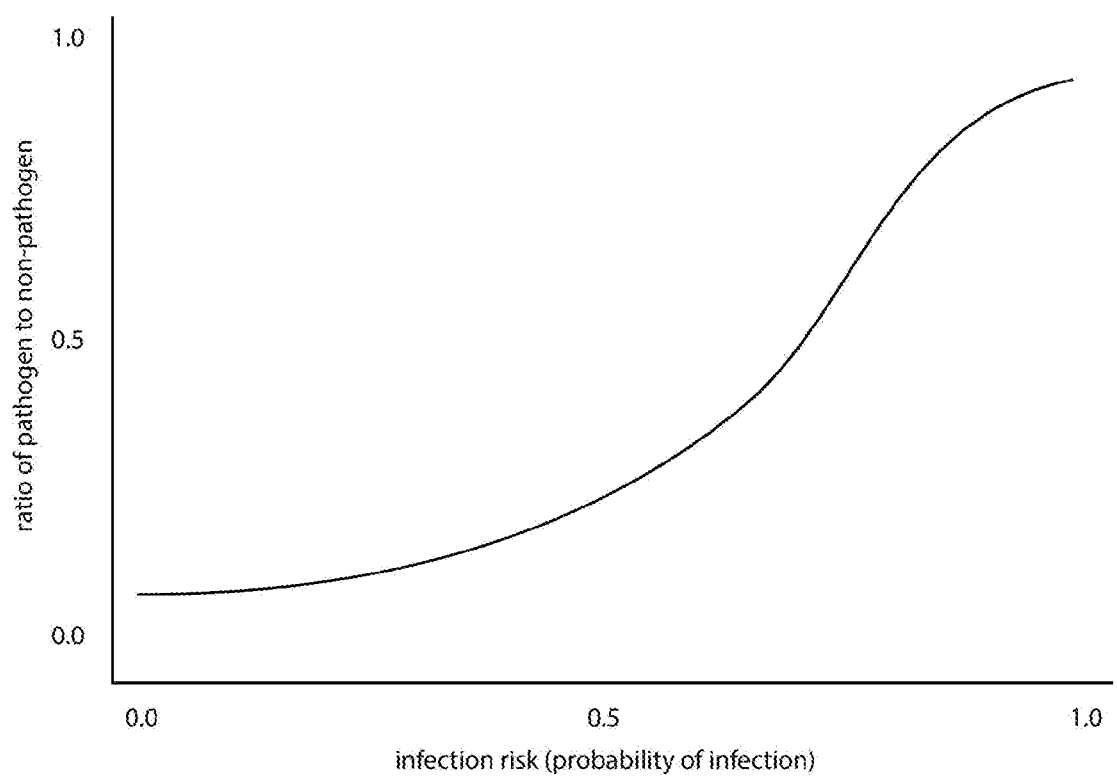
FIG. 4 is an illustration of the potential relationship between the pathogen ratio and infection risk. A statistical model of this relationship is built using Bayesian methods.
Figure 5:
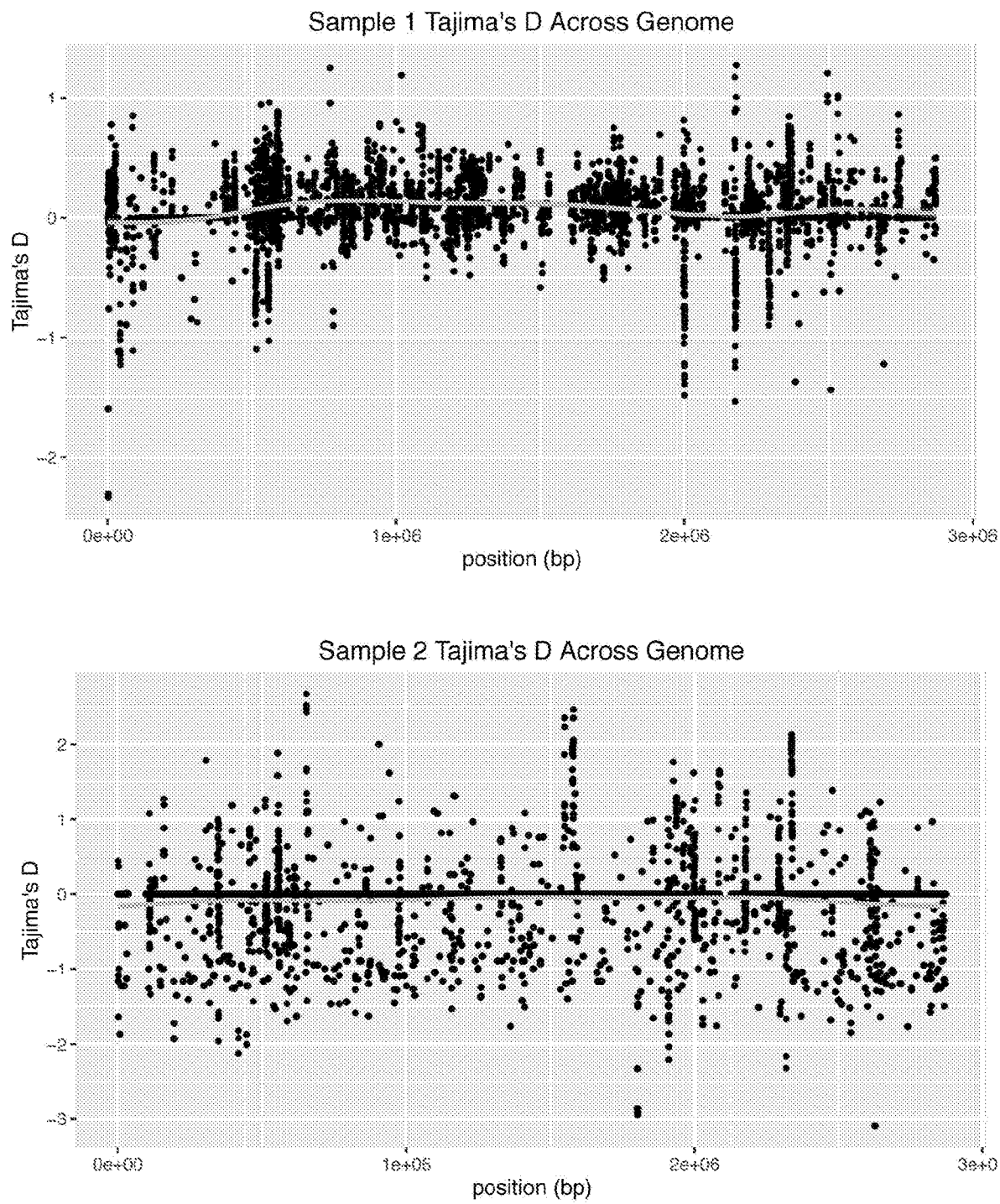
FIG. 5 depicts data plots for Tajima's D statistical analysis across *Staphylococcus aureus* genomes of real samples collected from ambulances, Sample 1 and Sample 2. As compared to Sample 1, Sample 2 harbors many negative outlier Tajima's D values (below −2) indicating positive selection at these loci and hence viability of the *S. aureus* population.

FIG. 1 is an illustration of the system disclosed with embodiment as a sequencing device (A), a system (B), and/or a software (C). The device may be portable or set up on site to rapidly characterize microbial populations in a subject sample or in the environment. Alternatively, the system may receive sequence data which the user collects from the environment or a subject, followed by sequencing and processing these data. In this case the system will include the capability of processing the sequence data using commercially available analysis tools including the ability to trim out poor quality reads, remove adapter sequences, use a kmer based or alternative approach for identification of microbes to the species or subspecies level, alignment of said species to references genomes or the ability to do de novo assembly. These results will then be further processed using the methods disclosed (C), which may be packaged as a software, to characterize viability and risk of transmission/infection. The disclosed methods include determining if a population of microbes is viable by comparing sequence data at multiple time points to see if a population is evolving (if it is evolving that indicates that it is viable) using a variety of population genetic inferences and by comparison to an outgroup (earlier time point) (FIG. 1 D, example graph of some population genetic inferences which might be calculated as depicted in FIGS. 3 and 5). This approach is described in more detail below. These methods also include characterizing the pathogenic nature of the identified species and strains and modeling these data using Bayesian models to assess risk of transmission and infection based on the ratio of commensal versus pathogenic organisms identified by matching to a database (FIG. 1 D, example graph of relationship to be modeled as depicted in FIG. 4). The system includes the ability to interact functionally with a remote data analysis center. This system may be capable of communicating via a network with relevant entities.

Sequence data will be analyzed at multiple time points using population genetic estimates to assess whether a population is viable (viability will be indicated by evolution by natural selection). There are multiple mechanisms for evolution and the disclosed system and methods will incorporate algorithms to differentiate between these mechanisms of migration, selection, drift, and mutation. Algorithms will also be included to differentiate between sequencing error as well as demographic and selection signals.

The precise location that environmental samples are collected from will be marked to ensure that samples will be collected from the same location at multiple time points. For example, in hospitals where high touch surfaces will be swabbed, the exact location might be marked using a permanent UV marking pen marker and revealed for subsequent collections by using a UV light. It is also possible that other technology will be employed to mark collection locations, including augmented reality.

For microorganisms in a sample for which there is sufficient sequence coverage and uniqueness, the method to determine viability and risk may involve calculating population genetic parameters using complementary approaches, at specific loci as well as across the genome (especially for single microorganismal samples which present less challenges than metagenomics samples in aligning reads to a reference genome) using a sliding windowed analysis (such as in FIG. 5). Metrics calculated may include nucleotide diversity ($\theta\pi$), genetic variance ($\theta_{Waterson}$), evidence of selection (Tajima's D; FIG. 5), genetic differentiation by comparing specific loci or windows at multiple time points ($F_{ST}$) with early time points also used as an outgroup to model population expansion and evolution. A database may be built to include markers of the most unique regions of species genomes, which will be used as markers to target in these viability analyses to sidestep the considerable challenge of correctly aligning metagenomics samples and misinterpretation of misalignments that occur due to sequence similarity between species. Complementary estimates will be calculated to determine if there is evidence to indicate mechanisms of evolution at work including migration, and natural selection and to differentiate between selection and demographic signals. To calculate these parameters, existing models will be modified to implement unbiased estimates of pooled samples (since metagenomic data is pooled by its nature) and to account for sequencing errors. For pooled sample analysis, a minimum coverage cutoff will be employed to ensure that SNPs called are truly SNPs and not sequencing errors. The methods will use a Bayesian approach to implement these models and increase the robustness of models over time as more data is collected and analyzed by using a statistical machine learning approach.

To estimate nucleotide diversity and genetic variance, population genetic parameters ($\theta\pi$) and ($\theta_{Waterson}$) are commonly used to calculate estimates for the sequencing of individuals. Modified versions of these estimates are used as described herein, to include unbiased estimates for metagenomics samples (which are by their nature pooled) are used with pool size n and coverage C:

$$\theta_{\pi_b,pool} = \frac{\theta_{\pi_b}}{c_n \sum_{m=b}^{C-b} \theta_\pi(m) \sum_{r=1}^{n-1} P(X_C = m \mid Y_n = r) P(Y_n = r)} \text{ and}$$

$$\theta_{W_b,pool} = \frac{\theta_{W_b} c_C}{c_n \sum_{m=b}^{C-b} \sum_{r=1}^{n-1} P(X_C = m \mid Y_n = r) P(Y_n = r)}.$$

Furthermore, $$c_n = \sum_{k=1}^{} \frac{1}{k}, P(X_C = m \mid Y_n = r)$$

is the probability of having allele frequency m among the reads given an allele frequency r in the pool and $P(Y_n=r)$ is the probability that an allele has frequency r in the pool.

These estimates are evaluated on SNPs with minimum allele count of b.

To estimate selection, a modified version of the class summary statistic Tajima's D (FIG. 5) is used. The modification allows for analysis of pooled data. This estimate characterizes deviations from the null model of a constant size population without selection.

$$D_{b,pool} = \frac{d_{b,pool}}{\sqrt{\text{Var}(d_{b,pool})}}$$

with $$d_{b,pool} = \theta_{\pi_b,pool} - \theta_{W_b,pool} \text{ and}$$

$$\text{Var}(d_{b,pool}) = E[(d_{b,pool})^2] = \theta c_n \sum_{m=b}^{C-b} (d_{b,pool}(m))^2 \sum_{r=1}^{n-1} P(X_C = m \mid Y_n = r) P(Y_n = r),$$

wherein $\theta$ is estimated by $$\theta_{\pi_b,pool}$$

in the same window in which $D_{b,pool}$ is calculated. Hereby we assume that all individuals contribute roughly equal amounts of DNA to the pool.

Estimates calculated as outlined above are used to calculate other indices to measure evolution, including $F_{ST}$ which in a simple form may be calculated as follows, but using the modified ($\theta\pi$) described above:

$$F_{ST} = \frac{\pi_{Between} - \pi_{Within}}{\pi_{Between}}$$

Where $\pi_{Between}$ and $\pi_{Within}$ represent the average number of pairwise differences between two individuals (or for pooled samples may be a subset of reads) from the same sample ($\pi_{Within}$) or from different samples ($\pi_{Between}$). Also, a more involved analysis may take place including conducting an analysis of molecular variance.

Additionally, a complementary approach may be used and a hierarchical Bayesian model may be built to quantify population structure and statistically identify regions of the genome which are affected by selection. This model is run to differentiate between demographic and selection signals and uses molecular divergence between populations or time points to identify regions under selection. For example, a model similar to the following may be employed. In this model, the probability of the observed haplotype frequencies given the population frequencies is described by a multivariate Polya distribution:

$$P(x \mid p, v) = \prod_i \prod_j \frac{n_{ij}!}{\prod_k (x_{ijk}!)} \frac{\Gamma\left(\sum_k v_j p_{ijk} + 1\right)}{\Gamma\left(n_{ij} + \sum_k v_j p_{ijk} + 1\right)} \times \prod_k \frac{\Gamma(x_{ijk} + v_j p_{ijk} + 1)}{\Gamma(v_j p_{ijk} + 1)}$$

where $n_{ij}$ is the total number of observed sequences at locus i for population j, and $x_{ij}k$ and $p_{ijk}$ are the observed count and population frequency of the kth haplotype in the jth population at the ith locus. The multinomial likelihood model assumes Hardy-Weinberg equilibrium for each locus and linkage equilibrium among loci.

Additionally, $\Gamma$ is the gamma function, $v_j$ is the number of gene copies sampled from population j, x is the observed haplotype counts, p is haplotype frequency, FIG. 3 is an illustration of theoretical results which would provide evidence that an area of a genome (between 1533000 bp and 1534000) is under selection. For this figure selection is indicated by the increase in $F_{ST}$ when calculated between 2 time points (increased differentiation), and reduction in He (expected heterozygosity or genetic variation) from the early time point to the later time point. This pattern indicates a selective sweep in the genome. Since this figure only describes the data at one locus but does not determine if the population is evolving, a model may be trained using experimentation in the lab where mixed populations of bacteria will be killed and kept alive at different concentrations and sequenced at multiple time points to determine confidence intervals to use similar data generated across the genome of the population (in the case of metagenomics the pooled individuals) to determine if a population is viable.

Additional calculations may be used to measure evolution including comparing sequence data and genomic variation collected from multiple time points. Accumulation of SNPs between time points may be used to estimate evolutionary rate. This accumulation may be measured across the genome, when possible or at loci which are unique between species, especially for regions which display high mutation rates such as mutation hotspots.

The dN/dS is also measured, across the genome when appropriate, or at specific loci, which is a commonly used population genetic estimate which measures substitution at synonymous (or silent sites-dS) versus non-synonymous (or non-silent sites-dN). Synonymous mutations do not result in changes at the protein level, whereas non-synonymous mutations may result in protein level changes which natural selection could act upon. Deviation from unity may indicate positive (dN/dS>1) or negative (dN/dS<1) selection operating at the protein level, which is evidence of evolution by selection. As described herein, deviation from unity provides support for the population being viable.

These calculations may be computed on individual microbes or pooled populations of microbes (as found in metagenomic samples) and different algorithms may be used to calculate these alternative sample types. Abundance estimates calculated using currently available tools will be incorporated into algorithm to parameterize number of individuals pooled. Populations which show evidence of selection (e.g., selective sweeps) which can be differentiated from demographic signatures (e.g., a drastic reduction in population size and genome-wide reduction in nucleotide diversity) will be reported as having a higher probability of being viable.

For analysis of antibiotic resistant loci and other loci deemed to be of interest, population genetic estimates will be calculated and statistical significance determined. One way that significance may be determined is by comparing the test distributions to null distributions created by resampling the dataset with replacement 1000 times. The test distribution will be regressed on the null distribution, and p values for the residuals will be calculated and subjected to a false discovery rate correction to account for multiple testing. Associated q values will be used and reported using a significant cutoff of 0.05 which indicates that only 5% of the outlier genes detected could be false positives.

One aspect of this invention may involve characterizing the genetic variation using linkage disequilibrium (LD) estimates, which can be impossible when conducting metagenomics using short sequencing reads. One way to circumvent this problem will be to use new technology which allows for the sequencing of much longer reads (up to tens of kilobases) since LD information is contained within each sequence read.

While understanding the consequences of demographic shifts and evolutionary processes is still a challenge which is increased when analyzing metagenomic data, it is possible to train models to give reliable estimates of important population genetic parameters as more pertinent data is generated.

Also disclosed is a method to identify infection risk based on obtaining a sample, extracting nucleic acids from the sample, sequencing and identifying strains, and determining the ratio of commensal to pathogenic microorganisms. The relationship between ratios of pathogenic strains to nonpathogenic strains will be modelled for important pathogens. The method disclosed builds on ecological principles including competition. Virulence markers will help to determine ratio of commensal versus pathogenic species/strains in addition to matching sequence and species identity to publicly available and proprietary pathogenicity databases. These data will be amassed into a new database which will be improved over time as more data is collected. This approach implements the ecological concept that areas of low microbial abundance and diversity may be suitable for opportunistic pathogens to grow and establish both on surfaces and in the body and that beneficial bacteria may competitively inhibit or directly fight off pathogenic bacteria. A Bayesian model will be developed to model the relationship between ratio of pathogenic to nonpathogenic organism and infection risk (one potential relationship illustrated in FIG. 4) and will incorporate environmental factors, medical records of patients, infection rates, sequence data and identification and ratio of microbes.

Inferential statistical analyses of the genomic data may be combined with environmental and medical observations to further interpret results of this system and methods. This approach may be used to make recommendations to the appropriate entities to combat pathogens identified, such as recommendations on specific cleaning products to use, or the use of other preventative strategies and/or empiric antimicrobial therapy.

The processor (FIG. 1) could be an application-specific integrated circuit designed to achieve one or more specific functions or enable one or more specific devise or applications. The processor can receive DNA sequence data to be stored in a data store in memory. The data store can also include any suitable types or forms of memory for storing data in a form retrievable by the processor.

This system could also include a communication component to which the processor can send data retrieved from the data store. The communication component can include any suitable technology for communicating with the communication network, such as wired, wireless, satellite, etc. The system can communicate via a communication network (FIG. 1) with a variety of entities that may be relevant to notify in the event of a bioterrorist act or an epidemic outbreak. These entities can include a First Responder, Center for Disease Control (CDC), physicians, public health personnel, law enforcement and others.

Methods of Micro-Organismal Characterization

The methods and systems described in the current invention may use the shortest unique sequence information, which in a mixture of nucleic acids in an uncharacterized sample have the minimal unique length (n) with respect to the entire sequence information generated or collected. In addition to unique length sequences, non-unique may also be compared. The probability of identification of a genome increases with multiple matches. Some genomes will have longer minimal unique sequences than other genomes. The matching method of short length (n) sequences may continue in parallel with sequence information generation or collection. The comparisons occur as fast as (real-time) subsequent longer sequences are generated or collected. This results in considerable decision space reduction because the calculations are made early in terms of sequence information generation/collection. The probabilistic matching may include, but is not limited to, perfect matching, subsequence uniqueness, pattern matching, multiple subsequence matching within n length, inexact matching, seed and extend, distance measurements and phylogenetic tree mapping. It may provide an automated pipeline to match the sequence information as fast as it is generated or in real-time. The sequencing instrument can continue to collect longer and more strings of sequence information in parallel with the comparison. Subsequent sequence information can also be compared and may increase the confidence of a genome or species identification in the sample. The method does not need to wait for sequence information assembly of the short reads into larger contigs.

In some embodiments, the system and methods may provide nucleic acid intake, isolation and separation, DNA sequencing, database networking, information processing, data storage, data display, and electronic communication to speed the delivery of relevant data to enable diagnosis or identification of organisms with applications for pathogenic outbreak and appropriate responses. In these embodiments, the system may include a portable sequencing device that electronically transmits data to a database for identification of organisms related to the determination of the sequence of nucleic acids and other polymeric or chain type molecules and probabilistic data matching. Embodiments include methods based on, but not limited to, Sequencing-by-synthesis, Sequencing-by-ligation, Single-molecule-sequencing and Pyrosequencing.

Probabilistic Methods and Techniques

In some embodiments, the present invention provides for systems and methods which employ a variety of probability-based techniques, models, and algorithms for determining the viability and risk of infection posed by any micro-organism present in a sample.

Probabilistic Classification: The present invention may provide database engines, database design, filtering techniques and the use of probability theory as Extended Logic. The instant methods and system may utilize the probability theory principles to make plausible reasoning (decisions) on data produced by nucleic acid sequencing. Using the probability theory approach, the system described herein may analyze data as soon as it reaches a minimal number of nucleotides in length (n), and calculating the probability of the n-mer, further each subsequent increase in length (n+base pair(s)) is used to calculate the probability of a sequence match. The calculation of each n-mer and subsequent longer n-mers may be further processed to recalculate the probabilities of all increasing lengths to identify the presence of genome(s). As the unit length increases, multiple sub-units, within the n-mer are compared for pattern recognition, which further increases the probability of a match. Such method, including other Bayesian methods, provides for eliminating matches and identifying a significant number of biological samples comprising with a very short nucleotide fragment or read without having to complete full genome sequencing or assembling the genome. As such, assigning the likelihood of the match to existing organisms and move on to the next nucleic acid sequence read to further improve the likelihood of the match.

Probabilistic methods may also be used to build and query databases of genetic markers, including databases of the most unique regions of species genomes, antibiotic resistance genes, virulence genes and phylogenetic markers. A probabilistic based statistical scoring approach may be used to assess matches between sample sequence and database, using a statistical score which represents the probability that a sequence match is a random occurrence based on the number of the total abundance of matches in the experimental spectrum.

Probability-based techniques underlie many of the population genetics models which will be utilized in this invention. For example, if $M_A$ ($M_a$) denotes the number of times allele A ($a$) is sequenced, given that $L_A=1$ of k individuals in the sample have an allele of type A, the probability of detecting polymorphism is equal to the probability of reading at least one of the A and one of the remaining a alleles in the sample. Assuming that for each individual the number of reads at a particular locus is Poisson distributed with parameter $\lambda$, the probability of not covering the SNP locus for an individual is $\exp(-\lambda)$. This leads to the following probability for getting at least one A and one a read.

$$q_c(l,k,\lambda) := (1-[\exp(-\lambda)]^l)(1-[\exp(-\lambda)]^{k-l})$$

In order to build probabilistic classifiers to make a decision on short nucleic acid sequences, a variety of approaches to first filter and later classify the incoming sequencing data can be utilized. In the instant case, the formalism of Bayesian networks is utilized. A Bayesian network is a directed, acyclic graph that compactly represents a probability distribution. In such a graph, each random variable is denoted by a node (for example, in a phylogenetic tree of an organism). A directed edge between two nodes indicates a probabilistic dependency from the variable denoted by the parent node to that of the child. Consequently, the structure of the network denotes the assumption that each node in the network is conditionally independent of its non-descendants given its parents. To describe a probability distribution satisfying these assumptions, each node in the network is associated with a conditional probability table, which specifies the distribution over any given possible assignment of values to its parents. In this case a Bayesian classifier is a Bayesian network applied to a classification task of calculating the probability of each nucleotide provided by any sequencing system. At each decision point the Bayesian classifier can be combined with a version of shortest path graph algorithm such as Dijkstra's or Floyd's.

The current system may implement a system of Bayesian classifiers (for example, Naïve Bayesian classifier, Bayesian classifier and Recursive Bayesian estimation classifier) and fuse the resulting data in the decisions database. After the data is fused, each classifier may be fed a new set of results with updated probabilities.

Algorithms and Filters

Taxonomy Filter: Taxonomy filter has two main tasks: (i) Filter out as many organisms as possible to limit the classifier module to a smaller decision space, and (ii) Help determine the structure of the Bayesian network, which involves the use of machine learning techniques.

Phylogenetic tree filter: This sub-module of taxonomy filter interfaces with "Decisions Database" to learn the results of the previous round of analysis. If no results are found the module passes the new data to classification module. If the results are found the taxonomy filter adjusts classifier data to limit the possible decision space. For example if the prior data indicates that this is a virus DNA sequence that is being looked at, the decision space for the classifier will be shrunk to viral data only. This can be done by modifying the data Bayesian classifiers collected while operating.

Machine Learning: Machine learning algorithms are organized into a taxonomy, based on the desired outcome of the algorithm. (i) Supervised learning in which the algorithm generates a function that maps inputs to desired outputs. One standard formulation of the supervised learning task is the classification problem: the learner is required to learn (to approximate) the behavior of a function which maps a vector [X1, X2, . . . XN] into one of several classes by looking at several input-output examples of the function. (ii) Semi-supervised learning which combines both labeled and unlabeled examples to generate an appropriate function or classifier. (iii) Reinforcement learning in which the algorithm learns a policy of how to act given an observation of the world. Every action has some impact in the environment, and the environment provides feedback that guides the learning algorithm. (iv) Transduction predicts new outputs based on training inputs, training outputs, and test inputs which are available while training. (v) Learning to learn in which the algorithm learns its own inductive bias based on previous experience.

Taxonomy Cache Module: The module caches taxonomy information produced by taxonomy filter. It can act as an interface between taxonomy filter and taxonomy database which holds all of the information in SQL database. Taxonomy cache is implemented as in-memory database with micro-second response timing. Queries to the SQL database are handled in a separate thread from the rest of the sub-module. Cache information includes the network graph created by the taxonomy filter module. The graph contains the whole taxonomy as the system starts analysis. DNA sequence analysis reduces the taxonomy graph with taxonomy cache implementing the reductions in data size and the removal of the appropriate data sets.

Classifier Selector: The instant system can utilize multiple classification techniques executing in parallel. Classifier selector can act as data arbiter between different classification algorithms. Classifier selector reads information from the Decisions Database and push such information to the classification modules with every DNA sequencing unit received for analysis from DNA Sequencing Module. Taxonomy filter acts as data pass through for the DNA sequencing data.

Recursive Bayesian Classifier: Recursive Bayesian classifier is a probabilistic approach for estimating an unknown probability density function recursively over time using incoming measurements and a mathematical process model. The module receives data from classifier selector and from the Decisions Database where prior decisions are stored. The data set is retrieved from the databases and prior decision identification placed in local memory of the module where the filtering occurs. The classifier takes DNA sequence and tries to match it with or without existing signatures, barcodes, etc., from the taxonomy database by quickly filtering out families of organisms that do not match. The algorithm works by calculating the probabilities of multiple beliefs and adjusting beliefs based on the incoming data. Algorithms used in this module may include Sequential Monte Carlo methods and sampling importance resampling. Hidden Markov Model, Ensemble Kalman filter and other particle filters may also be used together with Bayesian update technique.

Naëve Bayesian Classifier: Simple probabilistic classifier based on the application of the Bayes' theorem. The classifier makes all decisions based on the predetermined ruleset which is provided as user input at start-up. The module can be re-initialized with a new rule set while it is executing analysis. New rules set can come from the user or it can be a product of the rules fusion of The Results Fusions module.

Bayesian Network Classifier: Bayesian Network Classifier implements a Bayesian network (or a belief network) as a probabilistic graphical model that represents a set of variables and their probabilistic independencies.

Decisions Database: Decisions Database is a working cache for most modules in the system. Most modules have direct access to this resource and can modify their individual regions. However only Results Fusion module can access all data and modify the Bayesian rule sets accordingly.

Bayesian Rules Data: The module collects all Bayesian rules in binary, pre-compiled form. The rules are read-write to all Bayesian classifiers as well as Taxonomy Filter and Results Fusions modules. The rules are dynamically recompiled as changes are made.

Results Fusion: The module fuses the date from multiple Bayesian classifiers as well as other statistical classifiers that are used. Results Fusion module looks at the mean variance between generated answers for each classifier and fuses the data if needed.

Database Interface: Interface to the SQL database. The interface is implemented programmatically with read and write functions separated in different threads. MySQL is the database of choice however sqLite may be used for faster database speed.

Taxonomy Database: The database will hold multiple internal databases: taxonomy tree, indexed pre-processed tree, user input and rules.

Cached Rules In-Memory cache of post-processed rules provided by the user.

Rules Management: Graphical Management Interface to the Module

User Input: User created inference rules. The rules are used by Bayesian classifiers to make decisions.

The systems and methods of the invention are described herein as being embodied in computer programs having code to perform a variety of different functions. The code may be embodied on a non-transitory computer readable medium. Particular best-of-class technologies (present or emerging) can be licensed components. Existing methods for the extraction of DNA include the use of phenol/chloroform, salting out, the use of chaotropic salts and silica resins, the use of affinity resins, ion exchange chromatography and the use of magnetic beads. Methods are described in U.S. Pat. Nos. 5,057,426, 4,923,978, EP Patents 0512767 A1 and EP 0515484B and WO 95/13368, WO 97/10331 and WO 96/18731, the entire disclosures of which are hereby incorporated by reference. It should be understood, however, that the systems and methods are not limited to an electronic medium, and various functions can be alternatively practiced in a manual setting. The data associated with the process can be electronically transmitted via a network connection using the Internet. The systems and techniques described above can be useful in many other contexts, including those described below.

All viruses, bacteria and fungi contain DNA or RNA. The detection and sequencing of DNA or RNA from pathogens at the single molecule level could provide medically and environmentally useful information for the diagnosis, treatment and monitoring of infections and to predict potential drug resistance. Further opportunity will be in the arena of repeat-sequence applications where the methods are applied to the detection of subtle genetic variation.

Screening and Identification of Genome Sequences

The present invention is based, at least in part, on the ability to identify all, or nearly all, of the genomic sequences (including possible mutations and sequence variations) within a micro-organismal sample (e.g., mutations such as: translocations, inversions, large and small deletions and insertions, missense mutations, splice site mutations, etc.). In particular, these mutations or variations may be present in the genome of microorganisms of a sample, but not in normal colonies or the microorganisms. Such mutations are of particular interest if they lead to changes that result in a protein with an altered amino acid sequence that is unique to the microorganism's genome and subsequently affects viability and risk of infection. For example, useful mutations may include: (1) non-synonymous mutations leading to different amino acids in the protein; (2) read-through mutations in which a stop codon is modified or deleted, leading to translation of a longer protein with a novel tumor-specific sequence at the C-terminus; (3) splice site mutations that lead to the inclusion of an intron in the mature mRNA and thus a unique tumor-specific protein sequence; (4) chromosomal rearrangements that give rise to a chimeric protein with tumor-specific sequences at the junction of 2 proteins (i.e., gene fusion); (5) frameshift mutations or deletions that lead to a new open reading frame with a novel tumor-specific protein sequence; and the like. Peptides with mutations or mutated polypeptides arising from, for example, splice-site, frameshift, read-through, or gene fusion mutations in tumor cells may be identified by sequencing DNA, RNA or protein in samples versus control or reference samples.

A number of initiatives are currently underway to obtain sequence information directly from millions of individual molecules of DNA or RNA in parallel. Real-time single molecule sequencing-by-synthesis technologies rely on the detection of fluorescent nucleotides as they are incorporated into a nascent strand of DNA that is complementary to the template being sequenced. In one method, oligonucleotides 30-50 bases in length are covalently anchored at the 5' end to glass cover slips. These anchored strands perform two functions. First, they act as capture sites for the target template strands if the templates are configured with capture tails complementary to the surface-bound oligonucleotides. They also act as primers for the template directed primer extension that forms the basis of the sequence reading. The capture primers function as a fixed position site for sequence determination using multiple cycles of synthesis, detection, and chemical cleavage of the dye-linker to remove the dye. Each cycle consists of adding the polymerase/labeled nucleotide mixture, rinsing, imaging and cleavage of dye. In an alternative method, polymerase is modified with a fluorescent donor molecule and immobilized on a glass slide, while each nucleotide is color-coded with an acceptor fluorescent moiety attached to a gamma-phosphate. The system detects the interaction between a fluorescently-tagged polymerase and a fluorescently modified nucleotide as the nucleotide becomes incorporated into the de novo chain. Other sequencing-by-synthesis technologies also exist.

Preferably, any suitable sequencing-by-synthesis platform can be used to identify mutations or genomic sequences. Four major sequencing-by-synthesis platforms are currently available: the Genome Sequencers from Roche/454 Life Sciences, the HiSeq Analyzer from Illumina/Solexa, the SOLiD system from Applied BioSystems, and the Heliscope system from Helicos Biosciences. Sequencing-by-synthesis platforms have also been described by Pacific Biosciences and VisiGen Biotechnologies. Each of these platforms can be used in the methods of the invention. In some embodiments, a plurality of nucleic acid molecules being sequenced is bound to a support (e.g., solid support). To immobilize the nucleic acid on a support, a capture sequence/universal priming site can be added at the 3' and/or 5' end of the template. The nucleic acids may be bound to the support by hybridizing the capture sequence to a complementary sequence covalently attached to the support. The capture sequence (also referred to as a universal capture sequence) is a nucleic acid sequence complementary to a sequence attached to a support that may dually serve as a universal primer.

As an alternative to a capture sequence, a member of a coupling pair (such as, e.g., antibody/antigen, receptor/ligand, or the avidin-biotin pair as described in, e.g., U.S. Patent Application No. 2006/0252077) may be linked to each fragment to be captured on a surface coated with a respective second member of that coupling pair. Subsequent to the capture, the sequence may be analyzed, for example, by single molecule detection/sequencing, e.g., as described in the Examples and in U.S. Pat. No. 7,283,337, including template-dependent sequencing-by-synthesis. In sequencing-by-synthesis, the surface-bound molecule is exposed to a plurality of labeled nucleotide triphosphates in the presence of polymerase. The sequence of the template is determined by the order of labeled nucleotides incorporated into the 3' end of the growing chain. This can be done in real time or in a step-and-repeat mode. For real-time analysis, different optical labels to each nucleotide may be incorporated and multiple lasers may be utilized for stimulation of incorporated nucleotides.

Any micro-organismal cell may be utilized to obtain nucleic acid samples for use in the sequencing methods described herein. In a preferred embodiment, the DNA or RNA sample is obtained after extracting samples from a public environment (e.g., hospital, mall, park, etc.). Alternatively, nucleic acid tests can be performed on dry samples (e.g. hair or skin).

A variety of methods are available for detecting the presence of a particular mutation or allele in micro-organismal DNA or RNA. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

Polymerase Chain Reaction (PCR) and other Amplification Techniques

PCR based detection may include multiplex amplification of a plurality of markers simultaneously. For example, it is well known in the art to select PCR primers to generate PCR products that do not overlap in size and can be analyzed simultaneously. Alternatively, it is possible to amplify different markers with primers that are differentially labeled and thus can each be differentially detected. Of course, hybridization based detection means allow the differential detection of multiple PCR products in a sample. Other techniques are known in the art to allow multiplex analyses of a plurality of markers.

Several methods have been developed to facilitate analysis of single nucleotide polymorphisms in genomic DNA or cellular RNA. In one embodiment, the single base polymorphism can be detected by using a specialized exonuclease-resistant nucleotide, as disclosed, e.g., U.S. Pat. No. 4,656, 127. According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. Cohen et al. (French Pat. No. 2,650, 840; PCT Application No. WO1991/02087). As in the method of U.S. Pat. No. 4,656,127, a primer may be employed that is complementary to allelic sequences immediately 3' to a polymorphic site. The method determines the identity of the nucleotide of that site using labeled dideoxynucleotide derivatives, which, if complementary to the nucleotide of the polymorphic site, will become incorporated onto the terminus of the primer.

An alternative method, known as Genetic Bit Analysis or GBA® is described in PCT Application No. WO 1992/15712). GBA® uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Application No. WO1991/02087) the GBA® method is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779-7784 (1989); Sokolov, B. P., Nucl. Acids Res. 18:3671 (1990); Syvanen, A.-C, et al., Genomics 8:684-692 (1990); Kuppuswamy, M. N. et al., Proc. Natl. Acad. Sci. (U.S.A.) 88: 1143-1147 (1991); Prezant, T. R. et al., Hum. Mutat. 1: 159-164 (1992); Ugozzoli, L. et al., GATA 9: 107-112 (1992); Nyren, P. et al., Anal. Biochem. 208: 171-175 (1993)). These methods differ from GBA® in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A.-C, et al., Amer. J. Hum. Genet. 52:46-59 (1993)).

An alternative method for identifying changes in microbial viability and pathogenicity is direct protein sequencing. Protein sequencing of enzymatic digests using multidimensional MS techniques (MSn) including tandem mass spectrometry (MS/MS)) can also be used to identify microbial proteins of the invention. Such proteomic approaches permit rapid, highly automated analysis (see, e.g., K. Gevaert and J. Vandekerckhove, Electrophoresis 21: 1145-1154 (2000)). It is further contemplated within the scope of the invention that high-throughput methods for de novo sequencing of unknown proteins may be used to analyze the proteome of a micro-organismal sample to identify expressed proteins. For example, meta shotgun protein sequencing may be used to identify expressed proteins in a manner similarly applied to tumor antigens (see e.g., Guthals et al. (2012) Shotgun Protein Sequencing with Meta-contig Assembly, Molecular and Cellular Proteomics 11(10): 1084-96).

Peptide/Polypeptide Synthesis

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases located at the National Institutes of Health website. The coding regions for known genes may be amplified and/or expressed using the techniques disclosed herein or as would be known to those of ordinary skill in the art. Alternatively, various commercial preparations of proteins, polypeptides and peptides are known to those of skill in the art.

Peptides can be readily synthesized chemically utilizing reagents that are free of contaminating bacterial or animal substances (Merrifield R B: Solid phase peptide synthesis. I. The synthesis of a tetrapeptide. J. Am. Chem. Soc. 85:2149-54, 1963).

A further aspect of the invention provides a nucleic acid (e.g., a polynucleotide) encoding a microorganismal peptide of the invention, which may be used to produce the peptide in vitro. The polynucleotide may be, e.g., DNA, cDNA, PNA, CNA, RNA, either single- and/or double-stranded, or native or stabilized forms of polynucleotides, such as e.g. polynucleotides with a phosphorothiate backbone, or combinations thereof and it may or may not contain introns so long as it codes for the peptide. A still further aspect of the invention provides an expression vector capable of expressing a polypeptide according to the invention. Expression vectors for different cell types are well known in the art and can be selected without undue experimentation. Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host (e.g., bacteria), although such controls are generally available in the expression vector. The vector is then introduced into the host bacteria for cloning using standard techniques (see, e.g., Sambrook et al. (1989) Molecular Cloning, A Laboratory Manual, Cold Spring Harbor Laboratory, Cold Spring Harbor, N.Y.).

The invention further embraces variants and equivalents which are substantially homologous to the identified microorganismal protein described herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid, or one neutral amino acid by another neutral amino acid. What is intended by a conservative amino acid substitution is well known in the art.

The invention also includes expression vectors comprising the isolated polynucleotides, as well as host cells containing the expression vectors. It is also contemplated within the scope of the invention that the microorganismal peptides may be provided in the form of RNA or cDNA molecules encoding the desired neo-antigenic peptides. The invention also provides that the one or more microorganismal peptides of the invention may be encoded by a single expression vector. The invention also provides that the one or more microorganismal peptides of the invention may be encoded and expressed in vivo using a viral based system (e.g., an adenovirus system).

The term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In embodiments, the polynucleotides may comprise the coding sequence for the microorganismal peptide fused in the same reading frame to a polynucleotide which aids, for example, in expression and/or secretion of a polypeptide from a host cell (e.g., a leader sequence which functions as a secretory sequence for controlling transport of a polypeptide from the cell). The polypeptide having a leader sequence is a pre-protein and can have the leader sequence cleaved by the host cell to form the mature form of the polypeptide.

In embodiments, the polynucleotides can comprise the coding sequence for the microorganismal peptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In embodiments, the polynucleotides may comprise the coding sequence for one or more of the microorganismal peptides fused in the same reading frame to create a single concatamerized peptide construct capable of producing multiple peptides.

In embodiments, the present invention provides isolated nucleic acid molecules having a nucleotide sequence at least 60% identical, at least 65% identical, at least 70% identical, at least 75% identical, at least 80% identical, at least 85% identical, at least 90% identical, at least 95% identical, or at least 96%, 97%, 98% or 99% identical to a polynucleotide encoding a microorganismal peptide of the present invention.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The isolated microorganismal peptides described herein can be produced in vitro (e.g., in the laboratory) by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest will be inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors may be used to amplify and express DNA encoding the microorganismal peptides. Recombinant expression vectors are replicable DNA constructs which have synthetic or cDNA-derived DNA fragments encoding a microorganismal peptide or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., Cloning Vectors: A Laboratory Manual, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23: 175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine, maltose binding domain, influenza coat sequence, glutathione-S-transferase, and the like can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a protein composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Modified products can be detected directly, or after a further reaction which creates products which are easily distinguishable. Means which detect altered size and/or charge can be used to detect modified products, including but not limited to electrophoresis, chromatography, and mass spectrometry. Other means which are reliant on specific sequences can be used, including but not limited to hybridization, amplification, sequencing, and ligase chain reaction. Combinations of such techniques can be uses as is desired. Examples of such chemical reagents for selective modification include hydrazine and bisulfite ions. Hydrazine-modified DNA can be treated with piperidine to cleave it. Bisulfite ion-treated DNA can be treated with alkali.

The ability to monitor the real-time progress of the PCR changes the way one approaches PCR-based quantification of DNA and RNA. Reactions are characterized by the point in time during cycling when amplification of a PCR product is first detected rather than the amount of PCR product accumulated after a fixed number of cycles. The higher the starting copy number of the nucleic acid target, the sooner a significant increase in fluorescence is observed. An amplification plot is the plot of fluorescence signal versus cycle number. In the initial cycles of PCR, there is little change in fluorescence signal. This defines the baseline for the amplification plot. An increase in fluorescence above the baseline indicates the detection of accumulated PCR product. A fixed fluorescence threshold can be set above the baseline. The parameter $C_T$ (threshold cycle) is defined as the fractional cycle number at which the fluorescence passes the fixed threshold. For example, the PCR cycle number at which fluorescence reaches a threshold value of 10 times the standard deviation of baseline emission may be used as $C_T$ and it is inversely proportional to the starting amount of target cDNA. A plot of the log of initial target copy number for a set of standards versus $C_T$ is a straight line. Quantification of the amount of target in unknown samples is accomplished by measuring $C_T$ and using the standard curve to determine starting copy number.

The entire process of calculating $C_{TS}$, preparing a standard curve, and determining starting copy number for unknowns can be performed by software, for example that of the 7700 system or 7900 system of Applied Biosystems. Real-time PCR requires an instrumentation platform that consists of a thermal cycler, computer, optics for fluorescence excitation and emission collection, and data acquisition and analysis software. These machines, available from several manufacturers, differ in sample capacity (some are 96-well standard format, others process fewer samples or require specialized glass capillary tubes), method of excitation (some use lasers, others broad spectrum light sources with tunable filters), and overall sensitivity. There are also platform-specific differences in how the software processes data. Real-time PCR machines are available at core facilities or labs that have the need for high throughput quantitative analysis.

Briefly, in the Q-PCR method the number of target gene copies can be extrapolated from a standard curve equation using the absolute quantitation method. For each gene, cDNA from a positive control is first generated from RNA by the reverse transcription reaction. Using about 1 µl of this cDNA, the gene under investigation is amplified using the primers by means of a standard PCR reaction. The amount of amplicon obtained is then quantified by spectrophotometry and the number of copies calculated on the basis of the molecular weight of each individual gene amplicon. Serial dilutions of this amplicon are tested with the Q-PCR assay to generate the gene specific standard curve. Optimal standard curves are based on PCR amplification efficiency from 90 to 100% (100% meaning that the amount of template is doubled after each cycle), as demonstrated by the slope of the standard curve equation. Linear regression analysis of all standard curves should show a high correlation ($R^2$ coefficient .gtoreq.0.98). Genomic DNA can be similarly quantified.

When measuring transcripts of a target gene, the starting material, transcripts of a housekeeping gene are quantified as an endogenous control. Beta-actin is one of the most used nonspecific housekeeping genes. For each experimental sample, the value of both the target and the housekeeping gene are extrapolated from the respective standard curve. The target value is then divided by the endogenous reference value to obtain a normalized target value independent of the amount of starting material.

The term "primer" as used herein refers to a sequence comprising two or more deoxyribonucleotides or ribonucleotides, preferably more than three, and most preferably more than 8, which sequence is capable of initiating synthesis of a primer extension product, which is substantially complementary to a polymorphic locus strand. Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxy ribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

Primers of the invention are designed to be "substantially" complementary to each strand of the oligonucleotide to be amplified and include the appropriate nucleotides as discussed above. This means that the primers must be sufficiently complementary to hybridize with their respective strands under conditions that allow the agent for polymerization to perform. In other words, the primers should have sufficient complementarity with a 5' and 3' oligonucleotide to hybridize therewith and permit amplification of a nucleic acid sequence.

Primers of the invention are employed in the amplification process, which is an enzymatic chain reaction that produces exponentially increasing quantities of target locus relative to the number of reaction steps involved (e.g., polymerase chain reaction or PCR). Typically, one primer is complementary to the negative (−) strand of the locus (antisense primer) and the other is complementary to the positive (+) strand (sense primer). Annealing the primers to denatured nucleic acid followed by extension with an enzyme, such as the large fragment of DNA Polymerase I (Klenow) and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

The oligonucleotide primers used in invention methods may be prepared using any suitable method, such as conventional phosphotriester and phosphodiester methods or automated embodiments thereof. In one such automated embodiment, diethylphos-phoramidites are used as starting materials and may be synthesized as described by Beaucage, et al. (Tetrahedron Letters, 22:1859-1862, 1981). One method for synthesizing oligonucleotides on a modified solid support is described in U.S. Pat. No. 4,458,066.

The primers of the invention embrace oligonucleotides of sufficient length and appropriate sequence so as to provide specific initiation of polymerization on a significant number of nucleic acids in the polymorphic locus. Where the nucleic acid sequence of interest contains two strands, it is necessary to separate the strands of the nucleic acid before it can be used as a template for the amplification process. Strand separation can be effected either as a separate step or simultaneously with the synthesis of the primer extension products. This strand separation can be accomplished using various suitable denaturing conditions, including physical, chemical, or enzymatic means, the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP, is known to denature DNA. The reaction conditions suitable for strand separation of nucleic acids with helicases are described by Kuhn Hoffmann-Berling (CSH-Quantitative Biology, 43:63, 1978) and techniques for using RecA are reviewed in C. Radding (Ann. Rev. Genetics, 16:405-437, 1982).

As described herein, any nucleic acid specimen, in purified or nonpurified form, can be utilized as the starting nucleic acid or acids, provided it contains, or is suspected of containing, the specific nucleic acid sequence containing the target locus.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates to occur. Generally synthesis occurs in a buffered aqueous solution, preferably at a pH of 7-9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

The deoxyribonucleoside triphosphates dATP, dCTP, dGTP, and dTTP are added to the synthesis mixture, either separately or together with the primers, in adequate amounts and the resulting solution is heated to about 90 C.-100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

In certain preferred embodiments, the agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, polymerase muteins, reverse transcriptase, and other enzymes, including heat-stable enzymes (i.e., those enzymes which perform primer extension after being subjected to temperatures sufficiently elevated to cause denaturation). Suitable enzymes will facilitate combination of the nucleotides in the proper manner to form the primer extension products which are complementary to each locus nucleic acid strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2× SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Preferably, the method of amplifying is by PCR, as described herein and as is commonly used by those of ordinary skill in the art. Alternative methods of amplification have been described and can also be employed as long as the methylated and non-methylated loci amplified by PCR using the primers of the invention are similarly amplified by the alternative means.

The amplified products are preferably identified by sequencing. Sequences amplified by the methods of the invention can be further evaluated, detected, cloned, sequenced, and the like, either in solution or after binding to a solid support, by any method usually applied to the detection of a specific DNA sequence such as PCR, oligomer restriction, allele-specific oligonucleotide (ASO) probe analysis, oligonucleotide ligation assays (OLAs), and the like.

One may use MALDI mass spectrometry in combination with a detection assay to observe the size of a nucleic acid product. The principle behind mass spectrometry is the ionizing of nucleic acids and separating them according to their mass to charge ratio. Similar to electrophoresis, one can use mass spectrometry to detect a specific nucleic acid that was created in an experiment.

One form of chromatography, high performance liquid chromatography, is used to separate components of a mixture based on a variety of chemical interactions between a substance being analyzed and a chromatography column. DNA is first treated with sodium bisulfite, which converts an unmethylated cytosine to uracil, while methylated cytosine residues remain unaffected. One may amplify the region containing potential methylation sites via PCR and separate the products via denaturing high performance liquid chromatography (DHPLC). DHPLC has the resolution capabilities to distinguish between methylated (containing cytosine) and unmethylated (containing uracil) DNA sequences. (See Deng, D. et al. Simultaneous detection of CpG methylation and single nucleotide polymorphism by denaturing high performance liquid chromatography. 2002 Nuc Acid Res, 30, 3.)

Hybridization is a technique for detecting specific nucleic acid sequences that is based on the annealing of two complementary nucleic acid strands to form a double-stranded molecule. In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An additional method of sequencing would be to sequence the DNA to directly observe any modifications. Pyrosequencing technology is a method of sequencing-by-synthesis in real time. It is based on an indirect bioluminometric assay of the pyrophosphate (PPi) that is released from each deoxynucleotide (dNTP) upon DNA-chain elongation. This method presents a DNA template-primer complex with a dNTP in the presence of an exonuclease-deficient Klenow DNA polymerase. The four nucleotides are sequentially added to the reaction mix in a predetermined order. If the nucleotide is complementary to the template base and thus incorporated, PPi is released. The PPi and other reagents are used as a substrate in a luciferase reaction producing visible light that is detected by either a luminometer or a charge-coupled device. The light produced is proportional to the number of nucleotides added to the DNA primer and results in a peak indicating the number and type of nucleotide present in the form of a pyrogram. Pyrosequencing can exploit the sequence differences that arise.

A variety of amplification techniques may be used in a reaction for creating distinguishable products. Some of these techniques employ PCR. Other suitable amplification methods include the ligase chain reaction (LCR) (Barringer et al, 1990), transcription amplification (Kwoh et al. 1989; WO88/10315), selective amplification of target polynucleotide sequences (U.S. Pat. No. 6,410,276), consensus sequence primed polymerase chain reaction (U.S. Pat. No. 4,437,975), arbitrarily primed polymerase chain reaction (WO90/06995), nucleic acid based sequence amplification (NASBA) (U.S. Pat. Nos. 5,409,818; 5,554,517; 6,063,603), nick displacement amplification (WO2004/067726).

One way to distinguish between modified and unmodified DNA is to hybridize oligonucleotide primers which specifically bind to one form or the other of the DNA. After hybridization, an amplification reaction can be performed and amplification products assayed. The presence of an amplification product indicates that a sample hybridized to the primer. The specificity of the primer indicates whether the DNA had been modified or not. The amplification products can be optionally hybridized to specific oligonucleotide probes which may also be specific for certain products. Alternatively, oligonucleotide probes can be used which will hybridize to amplification products from both modified and nonmodified DNA.

Another way to distinguish between modified and non-modified DNA is to use oligonucleotide probes which may also be specific for certain products. Such probes can be hybridized directly to modified DNA or to amplification products of modified DNA. Oligonucleotide probes can be labeled using any detection system known in the art. These include but are not limited to fluorescent moieties, radio-isotope labeled moieties, bioluminescent moieties, luminescent moieties, chemiluminescent moieties, enzymes, substrates, receptors, or ligands.

Real time chemistry allows for the detection of PCR amplification during the early phases of the reactions, and makes quantitation of DNA and RNA easier and more precise. A few variations of the real-time PCR are known. They include the TAQMAN system and MOLECULAR BEACON system which have separate probes labeled with a fluorophore and a fluorescence quencher. In the SCORPION system the labeled probe in the form of a hairpin structure is linked to the primer.

Any specimen containing a detectable amount of polynucleotide or antigen can be used. Preferably the subject is human.

Samples

Samples for use in the methods of the invention include cells or tissues obtained from water, surfaces (i.e., walls, tables, beds, chairs, armrests, stools, counter-tops, instruments, screens, monitors, computers, floors, door handles, doors, windows, screens, pillows, cabinets, cabinet doors, sinks, faucets, etc.), blood, blood plasma, serum, cells, a cellular extract, a cellular aspirate, lung lavage, expectorant, sputum, saliva, mucous, urine, sweat, tears, and/or any bodily fluid.

Any nucleic acid specimen, in purified or nonpurified form, can be utilized as the starting nucleic acid or acids, provided it contains, or is suspected of containing, the specific nucleic acid sequence containing the target locus (e.g., genes or gene products related to determining viability and/or risk of causing infection). Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the target locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

The nucleic acid-containing sample or specimen used for detection of certain gene characteristics may be extracted by a variety of techniques such as that described by Maniatis, et al. (Molecular Cloning: A Laboratory Manual, Cold Spring Harbor, N.Y., pp 280, 281, 1982).

If the extracted sample is impure (e.g., plasma, serum, stool, ejaculate, sputum, saliva, ductal cells, nipple aspiration fluid, ductal lavage fluid, cerebrospinal fluid or blood or a sample embedded in paraffin), it may be treated before amplification with an amount of a reagent effective to open the cells, fluids, tissues, or animal cell membranes of the sample, and to expose and/or separate the strand(s) of the nucleic acid(s). This lysing and nucleic acid denaturing step to expose and separate the strands will allow amplification to occur much more readily.

Preferably, the method of amplifying is by PCR, as described herein and as is commonly used by those of ordinary skill in the art. However, alternative methods of amplification have been described and can also be employed. PCR techniques and many variations of PCR are known. Basic PCR techniques are described by Saiki et al. (1988 Science 239:487-491) and by U.S. Pat. Nos. 4,683,195, 4,683,202 and 4,800,159, each of which is incorporated herein by reference.

The conditions generally required for PCR include temperature, salt, cation, pH and related conditions needed for efficient copying of the master-cut fragment. PCR conditions include repeated cycles of heat denaturation (i.e. heating to at least about 95° C.) and incubation at a temperature permitting primer: adaptor hybridization and copying of the master-cut DNA fragment by the amplification enzyme. Heat stable amplification enzymes like the pwo, *Thermus aquaticus* or *Thermococcus litoralis* DNA polymerases which eliminate the need to add enzyme after each denaturation cycle, are commercially available. The salt, cation, pH and related factors needed for enzymatic amplification activity are available from commercial manufacturers of amplification enzymes.

As provided herein an amplification enzyme is any enzyme which can be used for in vitro nucleic acid ampli-fication, e.g. by the above-described procedures. Such amplification enzymes include pwo, *Escherichia coli* DNA polymerase I, Klenow fragment of *E. coli* polymerase I, T4 DNA polymerase, T7 DNA polymerase, *Thermus aquaticus* (Taq) DNA polymerase, Thermococcus litoralis DNA polymerase, SP6 RNA polymerase, T7 RNA polymerase, T3 RNA polymerase, T4 polynucleotide kinase, Avian Myeloblastosis Virus reverse transcriptase, Moloney Murine Leukemia Virus reverse transcriptase, T4 DNA ligase, *E. coli* DNA ligase or Q beta replicase. Preferred amplification enzymes are the pwo and Taq polymerases. The pwo enzyme is especially preferred because of its fidelity in replicating DNA.

Once amplified, the nucleic acid can be attached to a solid support, such as a membrane, and can be hybridized with any probe of interest, to detect any nucleic acid sequence. Several membranes are known to one of skill in the art for the adhesion of nucleic acid sequences. Specific non-limiting examples of these membranes include nitrocellulose (NITROPURE) or other membranes used in for detection of gene expression such as polyvinylchloride, diazotized paper and other commercially available membranes such as GENESCREEN, ZETAPROBE. (Biorad), and NYTRAN. Methods for attaching nucleic acids to these membranes are well known to one of skill in the art. Alternatively, screening can be done in a liquid phase.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2× SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. In general, conditions of high stringency are used for the hybridization of the probe of interest.

The probe of interest can be detectably labeled, for example, with a radioisotope, a fluorescent compound, a bioluminescent compound, a chemiluminescent compound, a metal chelator, or an enzyme. Those of ordinary skill in the art will know of other suitable labels for binding to the probe, or will be able to ascertain such, using routine experimentation.

Kits

The methods of the invention are ideally suited for the preparation of kits.

The invention features kits for identifying the viability of detected micro-organisms based upon certain gene characteristics, gene specific primers for use in polymerase chain reaction (PCR), and instructions for use. The invention also features kits for detecting the risk of a micro-organism causing infection. These kits may be used to process patient samples or samples collected from the environment. Environmentally targeted kits may include swabs which are optimized for maximum collection of sample off of surfaces, as well as release of said sample into buffer to facilitate downstream applications including extractions and purification of DNA, or RNA. Buffers may also be optimized to neutralize cleaning materials often found on hospital surfaces so these cleaning materials don't degrade the sample or interfere in downstream processes including extraction, purification, preparation for sequencing and sequencing. Environmentally targeted kits may also include a permanent UV marker and UV light to facilitate collection of sample at the same location at multiple time points. Additional tools may also be included in the kit to aid in sample collection and tracking including a mobile app which has augmented reality capabilities to mark sample collection locations.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

It should be appreciated that the invention should not be construed to be limited to the examples that are now described; rather, the invention should be construed to include any and all applications provided herein and all equivalent variations within the skill of the ordinary artisan.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Analysis of Environmentally Collected Samples by Counting SNPs Accumulated Over Time and Using dN/dS to Test for Viability Purpose: The use of SNP counts and population genetics algorithms to determine viability of a microbial species using genomic sequence data collected from the same surface at multiple time points, including day 1, and day 5.

For a single microorganismal (or a mix-microorganismal sample which has been processed to isolate a single species) sample, the whole genome (or metagenome) is analyzed using complementary approaches. One approach includes counting the accumulation of SNPs over time as well as the distribution of these SNPs at synonymous versus non-synonymous locations. This is determined by measuring the dN/dS ratio. Deviation from unity indicates positive (dN/dS>1) or negative (dN/dS<1) selection operating at the protein level, which is evidence of evolution by selection. As described herein, deviation from unity provides support for selection and indicates that the species is viable.

Results: Based on accumulation of up to 80 SNPs per day, as found in some strains of $E.\ coli$, up to 400 SNPs are seen across the genome by day 5, if the microbe is viable (this varies based on species and other factors). Since the $E.\ coli$ genome is about 4 Mb (varies based on strain) novel SNPs are about every 10,000 base pairs, if they are randomly accumulated, and dN/dS is 1. This mutation rate and sampling time frame is promising for accumulation of SNPs in order to measure viability as outlined herein. A dN/dS of 0.8 is considered a deviation from unity (confidence intervals are calculated based on lab work in which populations of microbes are grown for generations and sequenced at multiple time points in order to calculate dN/dS experimentally).

For this example, samples are collected by swabbing a surface on day 1 and day 5. Samples may be processed to isolate single microorganisms and identify them based on morphology or traditional microbiology techniques, although an alternative mixed-microorganismal pipeline characterized by a kmer-based or alignment based identification approach may be used instead. DNA is extracted and purified from isolated single microorganismal samples at the two time points, prepared for sequencing, and sequenced (see FIG. 1 A). Sequences are processed by trimming out low quality sequence as well as adapters. Cleaned up sequence data is aligned to the reference genome of species sequenced (FIG. 1 B). SNPs are called across the aligned genome and the ratio of synonymous versus non-synonymous mutations are calculated to get dN/dS for novel SNPs (FIG. 1 D). Novel SNPs are identified as polymorphisms present at day 5 which were absent at day 1 and are filtered based on coverage (sufficient coverage is required to make sure polymorphism is not in fact a sequencing error). Additional parameters may be calculated including algorithms which differentiate signals of selection versus demography. Viability of organisms are determined based on whether a minimum number of SNPs has accumulated and/or a dN/dS ratio deviating from unity. Containment protocols are implemented as needed based on findings.

Example 2

Analysis of Environmentally Collected Samples to Test for Viability Using Site Frequency Spectrum Analysis Purpose: Use population genetics algorithms related to site frequency spectrum analysis to determine viability of microbial species using genomic sequence data collected from the same surface at multiple time points, including day 1 and day 10.

For a single microorganismal or a mix-microorganismal sample, shotgun or long read sequencing of the whole genome is analyzed. One analysis approach includes aligning sequence reads to a reference genome followed by a windowed analysis to scan the alignment to estimate if areas of the genome experienced reduction or elimination of variation among nucleotides near a mutation site (selective sweep). Evidence of a selective sweep absent from an early time point but present at a later time point would indicate evolution by positive selection and therefore viability of microorganism (since population would need to be alive to evolve by positive selection). Site frequency spectrum analysis estimate Tajima's D may be used [Simonsen et al. 1995] to detect extreme outliers (<−2) which may indicate positive selection. Instead of using this commonly used outlier threshold of −2, outliers may be determined statistically. One way that significant outliers may be determined is by comparing the test distributions to null distributions created by resampling the dataset with replacement 1000 times. The test distribution will be regressed on the null distribution, and p values for the residuals will be calculated and subjected to a false discovery rate correction to account for multiple testing. Associated q values will be used and reported using a significant cutoff of 0.05 which indicates that only 5% of the outliers detected could be false positives.

Methods: These methods were tested using real data which is publicly available (SRA BioProject: PRJNA369713) that was collected from ambulances across the United States. For this available data, samples were collected from 398 ambulances, DNA was extracted and purified, library prep was conducted and samples were shotgun sequenced on an Illumina HiSeq 2500. Low quality sequences were removed (<Q20) and adaptors trimmed Data were then analyzed using available classification tools including MetaPhlAn [Segata et al, 2012] and CLARK [Ounit 2015]. To increase confidence in classification, the overlapping results between these two tools was used for further analysis. From this overlapping dataset, samples were selected that had positive hits for *Staphylococcus aureus* (N=15), an important nosocomial pathogen. For these samples, trimmed reads were mapped to an *S. aureus* reference genome (USA Strain GCA_000013465.1) using BWA. Tajima's D was calculated across the alignment using a sliding window approach (1 Kb windows). Tajima's D estimates for corresponding genomic locations were compared between samples. For the available ambulance data, samples were not collected at multiple time points, so spatial distance was used as a proxy for temporal distance, as is commonly done in evolutionary studies because genetic distance and differentiation accumulates both geographically and over time. The results of two samples and their comparison is presented here. These samples include a sample collected from Nevada (Sample 1) which will act as a proxy for time point 1 and another sample collected from Colorado (Sample 2) which will act as a proxy for time point 2.

Results: Coverage was sufficient across these samples to calculate population genetic estimates including Tajima's D (FIG. 5). There was no overall decrease in Tajima's D, signalling there was no bottleneck or overall reduction in genetic variation as indicated by the trend line hovering around zero (gray line). This pattern would indicate that the population has not been eliminated or dramatically reduced in size by cleaning or other factors (if the samples were in fact collected at 2 time points as illustrated). There was a significant decrease in Tajima's D at many specific loci providing evidence for positive selection. Additionally, only two loci were outliers (<−2) for Sample 1, while there were 37 outliers (<−2; although not all visible in figure because they are overlapping) for Sample 2. There was also a shift in range with the lowest Tajima's D value being −2.3 for Sample 1 and extending down to −3.1 for Sample 2. This indicates that (if these samples were collected from the same location at specific consecutive time points) that the *S. aureus* identified would be evolving and therefore viable.

Results from site frequency spectrum analysis address whether micoorganisms are alive (if evolving through positive selection then alive) and if specific functional loci, such as AMR are under positive selection which could indicate that a change in cleaning methods or antimicrobials is warranted. Containment protocols and alteration of protocols are implemented as needed based on findings.

What is claimed is:

1. A method of characterizing viability of one or more microorganism populations, comprising:

determining a DNA or RNA sequence of a genetic locus, loci, or genome from one or more microorganism populations in (i) a sample obtained from a location or source or (ii) multiple samples obtained from the same location or source at multiple time points;

comparing the DNA or RNA sequence to a reference database of genomic sequences to identify a microorganism and aligning the sequence to a reference locus or genome of the identified microorganism; and determining whether the one or more microorganism populations are evolving by a method comprising modeling genetic variation as allele distribution and changes in allele frequencies using population genetics statistics;

wherein a population is determined to be evolving where the allele distribution includes one or more of (1) a change in presence or absence of an allele between a first and subsequent time points; (2) an increase or decrease in one or more allele frequencies between a first and subsequent time points; and (3) a reduction or elimination of the genetic variation in a genomic region near a mutation site relative to the rest of the genome at a single time point; and wherein an evolving population is characterized as viable; and implementing a containment or treatment protocol based on the viability assessment.

2. The method of claim 1, wherein the one or more microorganism populations are selected from the group consisting of bacteria, fungi, viruses, protozoans, and parasites.

3. The method of claim 2, wherein the bacteria are selected from the phylogenetic group consisting of Acidobacteria, Actinobacteria, Aquificae, Armatimonadetes, Bacteroidetes, Caldiserica, Chlamydiae, Chlorobi, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermomicrobia, Thermotogae, and Verrucomicrobia.

4. The method of claim 2, wherein the bacteria are selected from the group consisting of *Acinetobacter baumannii, Actinomyces israelii, Bacillus anthracis, Bacillus cereus, Bacteroides fragilis, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens,*

*Clostridium tetani, Corynebacterium diphtheria, Ehrlichia canis, Ehrlichia chaffeensis, Enterococcus faecalis, Enterococcus faecium, Escherichia coli, Francisella tularensis, Haemophilus influenzae, Helicobacter pylori, Klebsiella pneumoniae, Legionella pneumophila, Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitides, Pseudomonas aeruginosa, Rickettsia rickettsia, Salmonella typhi, Salmonella typhimurium, Shigella sonnei, Shigella dysenteriae, Staphylococcus aureus, Staphylococcus epidermidis, Staphylococcus saprophyticus, Streptococcus agalactiae, Streptococcus pneumoniae, Streptococcus pyogenes, Streptococcus viridans, Treponema pallidum, Ureaplasma urealyticum, Vibrio cholera, Yersinia pestis, Yersinia enterocolitica,* and *Yersinia pseudotuberculosis.*

5. The method of claim 2, wherein the virus are selected from the group consisting of Adenovirus, Herpes simplex, type 1, Herpes simplex, type 2, Varicella-zoster virus, Epstein-barn virus, Human cytomegalovirus, Human herpesvirus, type 8, Human papillomavirus, BK virus, JC virus, Smallpox, Hepatitis B virus, Parvovirus B19, Human astrovirus, Norwalk virus, coxsackievirus, hepatitis A virus, poliovirus, rhinovirus, Hepatitis C virus, yellow fever virus, dengue virus, West Nile virus, TBE virus, Rubella virus, Hepatitis E virus, Human immunodeficiency virus (HIV), Influenza virus, Lassa virus, Crimean-Congo hemorrhagic fever virus, Hantaan virus, Ebola virus, Marburg virus, Measles virus, Mumps virus, Parainfluenza virus, Respiratory syncytial virus, Rabies virus, Rotavirus, Orbivirus, Coltivirus, Banna virus, and zika virus.

6. The method of claim 2, wherein the fungi are selected from the group consisting of *Candida* species, *Candida albicans, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii, Pneumocystis carinii,* and *Stachybotrys chartarum.*

7. The method of claim 2, wherein the protozoa are selected from the group consisting of *Entamoeba histolytica, Entamoeba coli, Entamoeba dispar, Entamoeba moshkovskii, Entamoeba bangladeshi, Entamoeba hartmanni, Dientamoeba fragilis, Endolimax nana, Iodamoeba butschlii, Plasmodium malariae, Plasmodium falciparum, Plasmodium vivax, Plasmodium ovale, Naegleria fowleri, Acanthamoeba species, Balamuthia mandrillaris, Sappinia diploidea, Giardia lamblia, Giardia intestinalis, Giardia duodenalis, Toxoplasma gondii, Nippostrongylus brasiliensis, Cryptosporidium parvum, Cryptosporidium hominis, Cryptosporidium canis, Cryptosporidium felis, Cryptosporidium meleagridis, Cryptosporidium muris, Trichomonas vaginalis, Trypanosoma cruzi, Leishmania major, Leishmania tropica, Leishmania barziliensis, Leishmania mexicana, Leishmania guyanesis, Leishmania panamensis,* and *Trypanosoma brucei.*

8. The method of claim 1, wherein the DNA or RNA sequence of a plurality of genomic fragments is obtained by massively parallel signature sequencing, Polony sequencing, 454 pyrosequencing, Illumina sequencing, SOLiD sequencing, ion semiconductor sequencing, DNA nanoball sequencing, heliscope sequencing, single molecule real time (SMRT) sequencing, nanopore sequencing, hybridization, amplicon-based sequencing, mass spectroscopy-based sequencing, Sanger sequencing, transmission electron microscopy sequencing, or quantum sequencing.

9. The method of claim 1, wherein the genetic variation is selected from the group consisting of single nucleotide polymorphisms, deletions, and insertions.

10. The method of claim 1, wherein the one or more genomic DNA regions are randomly selected or specifically targeted loci.

11. The method of claim 1, further comprising:
determining that the genetic variation at a specific location within the one or more genomic DNA regions is in synonymous or non-synonymous sites, wherein a preponderance of non-synonymous variation indicates evolution by natural selection and therefore viability of the one or more microorganism populations.

12. The method of claim 1, wherein the allele frequencies are modeled by site frequency spectrum analysis using Tajima's D statistical method.

13. The method of claim 1, wherein the allele frequency and distribution differences between the time points are modeled by fixation index (FST).

14. The method of claim 1, wherein the genetic locus or loci comprise one or more functional loci.

15. The method of claim 1, wherein the method comprises differentiating between sequencing error and demographic versus selection signals.

16. The method of claim 14, wherein the functional loci comprise one or more antimicrobial resistance loci.

17. The method of claim 1, further comprising implementing a containment protocol based on the viability assessment.

18. The method of claim 17, wherein the containment protocol is a Centers for Disease Control approved protocol.

19. The method of claim 1, wherein the sample is obtained from a surface.

20. The method of claim 1, wherein the sample is obtained from water.

21. The method of claim 1, wherein the sample is obtained from blood, plasma, serum, lung lavage, expectorant, sputum, saliva, mucous, urine, sweat, tears, or other bodily fluid.

22. The method of claim 1, wherein the sample is collected from the environment.

23. The method of claim 1, wherein the location is a high touch surface.

24. The method of claim 1, further comprising differentiating between modes of evolution selected from drift, selection, migration, and mutation and estimating a likelihood of evolution by natural selection.

25. The method of claim 12, wherein Tajima's D is calculated across aligned sequences using a sliding window analysis.

26. The method of claim 25, wherein the sliding window analysis is followed by outlier statistical analysis to estimate a likelihood of evolution by natural selection.

* * * * *